United States Patent [19]

Knight et al.

[11] Patent Number: 4,690,917

[45] Date of Patent: Sep. 1, 1987

[54] IMIDAZOPYRIDAYINE DERIVATIVES HAVING ANTIVIRAL ACTIVITY

[75] Inventors: David J. Knight, Chalfont St Peter; David I. C. Scopes, Furneux Pelham; Richard Storer, Pinner; Stuart Holman, Northolt, all of England

[73] Assignee: Glaxo Group Limited, London, England

[21] Appl. No.: 800,667

[22] Filed: Nov. 22, 1985

[30] Foreign Application Priority Data

Nov. 23, 1984 [GB] United Kingdom ............... 8429694

[51] Int. Cl.⁴ .................. A61K 31/70; C07H 3/02
[52] U.S. Cl. ........................... 514/23; 536/53; 536/55
[58] Field of Search ............. 536/53, 55; 514/23

[56] References Cited

U.S. PATENT DOCUMENTS

| | | | |
|---|---|---|---|
| 3,998,999 | 12/1976 | DeBernardo et al. | 536/55 |
| 4,092,472 | 5/1978 | Townsend et al. | 536/55 |
| 4,096,321 | 6/1978 | Weigele et al. | 536/55 |
| 4,584,369 | 4/1986 | Klein et al. | 536/55 |

*Primary Examiner*—Dolph H. Torrence
*Attorney, Agent, or Firm*—Bacon & Thomas

[57] ABSTRACT

Compounds of the formula:

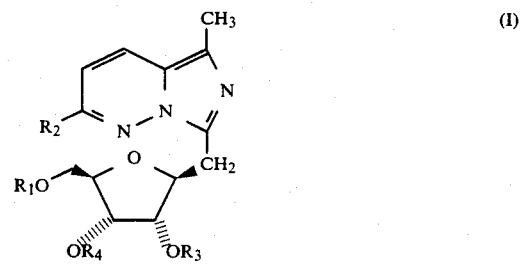

wherein
$R_1$, $R_3$ and $R_4$ each independently represents a hydrogen atom or a protecting group;
$R_2$ represents a halogen atom or a group of formula $-NR_a R_b$ (where $R_a$ and $R_b$, which may be the same or different, each represents a hydrogen atom or an alkyl group; or $R_a$ and $R_b$ may be linked to form, together with the nitrogen atom to which they are attached, a heterocyclic ring which optionally contains a further heteroatom);
and their physiological equivalents as well as salts thereof with acids, exhibit antiviral activity against RNA viruses such as Influenza and/or are intermeidates for the preparation of antivirally active compounds.

15 Claims, No Drawings

IMIDAZOPYRIDAYINE DERIVATIVES HAVING ANTIVIRAL ACTIVITY

This invention relates to new imidazopyridazine derivatives having antiviral activity.

Although the art of antibacterial chemotherapy is well advanced, there is no corresponding group of compounds which are active and effective against viral infections. Even against influenza, an infection of enormous economic importance, there are only a few compounds which have any useful activity. Amantadine and some related compounds have been used in the treatment of influenza, but their activity is restricted to Influenza A virus. Other compounds which are claimed to have activity against RNA viruses include ribavirin (1-$\beta$-D-ribo-furanosyl-1,2,4-triazole-3 carboxamide), DHP-Ade ((S)-9-(2,3-dihydroxypropyl)adenine) and Interferon; none of these has achieved any practical importance in the treatment of influenza. There is thus a need for further compounds showing activity against RNA viruses, particularly against Myxoviridae such as Influenza viruses.

In our British Patent Specification No. 1583911 we describe imidazo[1,5-b]pyridazines carrying inter alia an unsubstituted alkyl group at the 3-position (corresponding to the 7-position in the present compounds) which compounds exhibit cAMP phosphodiesterase inhibiting activity and are thus of use in the treatment of lung and peripheral vascular diseases. A ribofuranosylmethyl compound, homoshowdomycin, is described in Japanese Patent Application No. J57140715 as exhibiting antitumor activity.

We have now found that a group of new ribofuranosylmethyl-imidazo[1,5-b]pyridazine derivatives having low phosphodiesterase inhibiting activity exhibit interesting antiviral activity and in particular activity against RNA viruses including Myxoviridae e.g. the Influenza viruses.

According to one feature of the present invention, we provide compounds of the general formula (I)

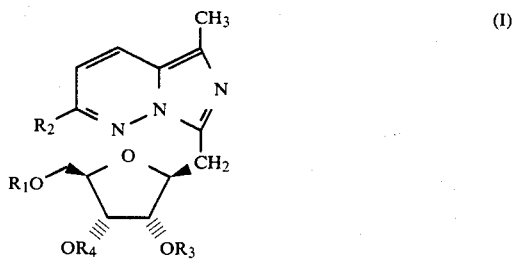

wherein
$R_1$, $R_3$ and $R_4$ each independently represents a hydrogen atom or a protecting group e.g. the group RCO wherein R represents a hydrocarbyl group containing up to 30 carbon atoms;
$R_2$ represents a halogen atom or a group of formula —$NR_a R_b$ (where $R_a$ and $R_b$, which may be the same or different, each represents a hydrogen atom or an alkyl group); or $R_a$ and $R_b$ may be linked to form together with the nitrogen atom to which they are attached, a heterocyclic ring which optionally contains a further heteroatom);
and their physiological equivalents as well as salts thereof with acids.

In the above formula (I) the methylene group carrying the base is in the $\beta$-configuration relative to the sugar ring. It will be appreciated that the use of the term $\beta$-configuration is not strictly accurate here because it does not refer to the configuration at the lowest numbered carbon. However the symbol is retained herein for clarity and pertains to the disposition of the groups across the anhydro linkage of the ribosyl ring i.e., $\beta$ is equivalent to cis.

The compounds of formula (I) may exist as optical isomers and the invention includes the separate enantiomers as well as all mixtures, including racemic mixtures, thereof.

The physiological equivalents of compounds of formula (I) are compounds which are converted in vivo into the parent compound of formula (I). Such compounds may include, for example, metabolically labile esters e.g. acetates and methoxyacetates.

The compounds of formula (I) and their physiological equivalents form salts with acids. It will be appreciated that, for pharmaceutical use, these salts will be physiologically acceptable but other salts may find use, for example, in the preparation of compounds of formula (I) and their physiological equivalents as well as of physiologically acceptable salts thereof. Physiologically acceptable salts of the compounds of formula (I) with acids include, for example, salts formed with hydrochloric, hydrobromic, nitric, sulphuric, phosphoric, acetic, formic, propionic, maleic, fumaric, succinic, tartaric, citric, glyoxylic and aspartic acid, arylsulphonic acids such as benzenesulphonic and p-toluenesulphonic acid and arylcarboxylic acids, e.g. benzoic acid.

When any of $R_1$, $R_3$ and $R_4$ is a protecting group, it may be any suitable protecting group e.g. as described hereinafter. Thus for example any of $R_1$, $R_3$ and $R_4$ may be an acyl group, such as a hydrocarbyl carbonyl group RCO.

The hydrocarbyl group R may include aliphatic hydrocarbyl such as straight chain or branched alkyl, alkenyl, alkynyl or cycloalkyl; aromatic hydrocarbyl; or aralkyl e.g. benzyl.

When the hydrocarbyl group R in the componds of formula (I) represents a straight or branched chain alkyl group it may be, for example a $C_{1-15}$ alkyl group such as methyl, ethyl, propyl, prop-2-yl, butyl, but-2-yl, pentyl or pent-3-yl. Groups of particular interest include n-hexyl, n-heptyl and n-octyl, especially n-heptyl.

An alkenyl or alkynyl group represented by the group R may be, for example, a straight or branched chain $C_{3-15}$ alkenyl or alkynyl group.

A cycloalkyl group represented by the group R may be a monocyclic or polycyclic cycloalkyl group, for example a $C_{3-7}$ monocyclic cycloalkyl group such as cyclopentyl, cyclohexyl or cycloheptyl or a $C_{9-22}$ polycyclic cycloalkyl group such as adamantyl, any of which may optionally be substituted by one or more alkyl groups of one or two carbon atoms.

An aromatic hydrocarbyl group represented by the group R may be, for example, a $C_{6-14}$ aryl group such as phenyl or naphthyl. The aromatic nucleus of the hydrocarbyl group may optionally be substituted by one or more alkyl groups of one or two carbon atoms.

An aralkyl group represented by the group R may be, for example, a $C_{7-10}$ aralkyl group, especially a phenyl-$C_{1-3}$ alkyl group such as benzyl.

Where $R_1$ represents the group RCO, the group R preferably contains 3 or more carbon atoms, especially 5 or more carbon atoms, e.g. 5 to 10 carbon atoms.

The group $R_2$ may be halogen, i.e. fluorine, chlorine, bromine or iodine, preferably chlorine, or the group $-NR_aR_b$ where $R_a$ and $R_b$ are independently hydrogen or alkyl groups containing, for example, 1 to 10 carbon atoms, e.g. 1–6 carbon atoms such as methyl, ethyl or propyl. When $R_a$ and $R_b$ are linked to form a heterocyclic ring optionally containing another heteroatom, such rings are optionally saturated and may contain e.g. 5, 6 or 7 ring members and if desired may comprise a further nitrogen or oxygen heteroatom. The ring may e.g. be pyrrolidino, piperidino, piperazino or morpholino. The heterocyclic ring may bear one or more $C_{1-2}$ alkyl substituents, e.g. methyl.

The compounds according to the invention are useful as intermediates for preparing active antiviral compounds.

Many compounds according to the invention have antiviral activity, especially against RNA viruses such as e.g. the Influenza viruses. Compounds of particular interest include those of the formula (Ia):

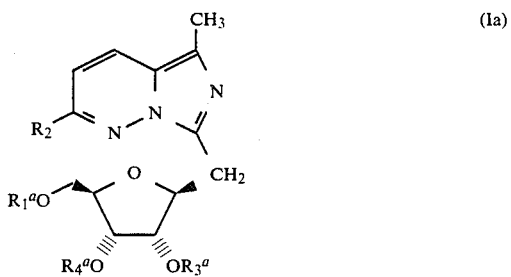

wherein at least one of $R_1{}^a$, $R_3{}^a$ and $R_4{}^a$ represents an acyl group of formula $R^aCO$ where $R^a$ represents a $C_{3-30}$ hydrocarbyl group except that when $R_2$ represents the group $NR_aR_b$, $R_1{}^a$, $R_3{}^a$ and $R_4{}^a$ may additionally all represent hydrogen atoms;

and their physiological equivalents as well as their physiologically acceptable salts.

The group $R^a$ may e.g. have the preferred values mentioned above for R in formula (I). A preferred class of active compounds is that wherein $R^a$ represents a $C_{5-10}$ alkyl, $C_{3-7}$ cycloalkyl, phenyl, naphthyl, adamantyl or phenyl-$C_{1-3}$ alkyl group.

A further preferred class of compounds is that wherein $R_2$ represents a chlorine or bromine atom or a group of formula $NR_aR_b$ (wherein $R_a$ represents a $C_{1-6}$ alkyl group and $R_b$ represents a hydrogen atom or a $C_{1-3}$ alkyl group or where $NR_a R_b$ represents a piperidino group).

A particularly preferred class of compounds according to the invention is that wherein $R_1{}^a$ is $R^aCO$, where $R^a$ represents a propyl, pentyl, hexyl, heptyl, octyl, cyclohexyl, adamantyl, phenyl, naphthyl or benzyl group and $R_2$ represents a chlorine or bromine atom or a ($C_{1-6}$ alkyl)amino or dimethylamino group or $NR_aR_b$ represents a piperidino group, and physiological equivalents and physiologically acceptable salts thereof.

Preferred compounds include:
7-(5'-O-benzoyl-β-D-ribofuranosylmethyl)-5-methyl-2-(methylamino)imidazo[1,5-b]pyridazine;
2-chloro-5-methyl-7-(5'-O-phenylacetyl-β-D-ribofuranosylmethyl)imidazo[1,5-b]pyridazine;
2-chloro-7-(5'-O-hexanoyl-β-D-ribofuranosylmethyl)-5-methylimidazo[1,5-b]pyridazine;
7-(5'-O-butanoyl-β-D-ribofuranosylmethyl)-2-chloro-5-methylimidazo[1,5-b]pyridazine;
2-chloro-7-[5'-O-(cyclohexanecarbonyl)-β-D-ribofuranosylmethyl]-5-methylimidazo[1,5-b]pyridazine;
7-[5'-O-(1-adamantanecarbonyl)-β-D-ribofuranosylmethyl]-2-chloro-5-methylimidazo[1,5-b]pyridazine;
2-chloro-7-[5'-O-(2-naphthoyl)-β-D-ribofuranosylmethyl]-5-methylimidazo[1,5-b]pyridazine;
7-(5'-O-benzoyl-β-D-ribofuranosylmethyl)-2-(dimethylamino)-5-methylimidazo[1,5-b]pyridazine;
7-(5'-O-benzoyl-β-D-ribofuranosylmethyl)-5-methyl-2-(N-pentylamino)imidazo[1,5-b]pyridazine;
7-(5'-O-benzoyl-β-D-ribofuranosylmethyl)-2-bromo-5-methylimidazo[1,5-b]pyridazine;
2-chloro-7-(5'-O-octanoyl-β-D-ribofuranosylmethyl)-5-methylimidazo[1,5-b]pyridazine;
2-(dimethylamino)-5-methyl-7-(β-D-ribofuranosylmethyl)imidazo[1,5-b]pyridazine;
7-(5'-O-benzoyl-β-D-ribofuranosylmethyl)-5-methyl-2-piperidinoimidazo[1,5-b]pyridazine,
7-(2'-O-benzoyl-β-D-ribofuranosylmethyl)-2-chloro-5-methylimidazo[1,5-b]pyridazine;
7-(3'-O-benzoyl-β-D-ribofuranosylmethyl)-2-chloro-5-methylimidazo[1,5-b]pyridazine;
7-(5'-O-benzoyl-β-D-ribofuranosylmethyl)-2-chloro-5-methylimidazo[1,5-b]pyridazine;
2-chloro-5-methyl-7-(2'-O-octanoyl-β-D-ribofuranosylmethyl)imidazo[1,5-b]pyridazine;
2-chloro-5-methyl-7-(3'-O-octanoyl-β-D-ribofuranosylmethyl)imidazo[1,5-b]pyridazine;
7-(2'-O-benzoyl-β-D-ribofuranosylmethyl)-5-methyl-2-piperidinoimidazo[1,5-b]pyridazine;
7-(3'-O-benzoyl-β-D-ribofuranosylmethyl)-5-methyl-2-piperidinoimidazo[1,5-]pyridazine;
and their physiological equivalents and physiologically acceptable salts.

Active compounds according to the invention have good activity against Influenza A virus in vitro (plaque reduction test). Further, many of the compounds which we have tested, including the preferred species listed above, have revealed no apparent cytotoxicity at antivirally effective levels.

A particularly preferred compound is 7-(5'-O-benzoyl-β-D-ribofuranosylmethyl)-2-chloro-5-methylimidazo[1,5-b]pyridazine and its physiological equivalents and physiologically acceptable salts. This compound has been found to be active in vivo against Influenza A and B viruses in mice, and was well tolerated at the antivirally effective dose.

The invention accordingly provides as a further feature active compounds of formula (I) and their physiological equivalents and physiologically acceptable salts thereof with acids for use in the therapy or prophylaxis of RNA viral infections, e.g. influenza, in a human or animal subject.

The active compounds according to the invention may be formulated for administration in any convenient way, and the invention therefore also includes within its scope pharmaceutical compositions comprising at least one active compound of formula (I) or a physiological equivalent or physiologically acceptable salt thereof in association with a pharmaceutical carrier or excipient adapted for use in human or veterinary medicine. Such compositions may be presented for use in conventional manner in admixture with one or more physiologically acceptable carriers or excipients. The compositions may optionally further contain one or more other therapeutic agents which may if desired be a different antiviral agent.

Thus, the active compounds according to the invention may be formulated for oral, buccal, parenteral, topical or rectal administration.

Tablets and capsules for oral administration may contain conventional excipients such as binding agents, for example, syrup, acacia, gelatin, sorbitol, tragacanth, mucilage of starch or polyvinyl pyrrolidone; fillers, for example, lactose, sugar, maize-starch, calcium phosphate or sorbitol; lubricants, for example, magnesium stearate, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The active compounds may also be formulated as suppositories, e.g. containing conventional suppository bases such as cocoa butter or other gylcerides.

For buccal administration the compositions may take the form of tablets or lozenges formulated in conventional manner.

The active compounds according to the invention may also be formulated for injection and may be presented in unit dose form in ampoules or in multidose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

For topical administration the active compounds according to the invention may be formulated as powders, pessaries, sprays, aerosols or drops (e.g. nose drops). Drops may be formulated with an aqueous or non-aqueous base also comprising one or more dispersing agents, solubilising agents or suspending agents.

For administration by inhalation, the active compounds are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator. Some form of continuous inhalation method may also be appropriate for, for example, serious respiratory tract infections.

The pharmaceutical compositions according to the invention may also contain other active ingredients such as antimicrobial agents, or preservatives.

The compositions may contain from 0.1–99% of the active material.

For administration by inhalation the daily dosage as employed for treatment of an adult human of approximately 70 kg body weight will range from 1 mg to 1000 mg, preferably 5 to 500 mg., which may be administered in single or multiple doses, 1 to 6 times a day or by continuous inhalation e.g. for 20 hours a day.

For systemic administration the daily dosage as employed for treatment of an adult human of approximately 70 kg body weight will range from 1 mg to 2 g, preferably 5 mg to 500 mg, which may be administered in 1 to 4 doses, for example, depending on the route of administration and the condition of the patient.

The compounds of the invention may be prepared by a number of processes which processes constitute a further feature of the invention.

Thus, according to one general process (A), the compounds of general formula (I) may be prepared by treating compounds of general formula (II)

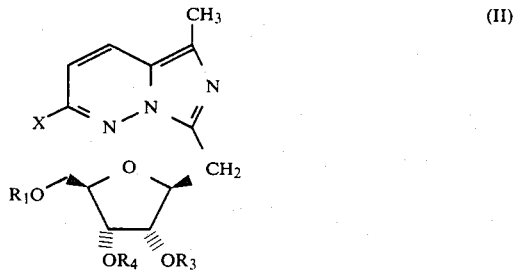

(II)

(wherein $R_1$, $R_3$ and $R_4$ are as defined above; and X represents a displaceable atom or group other than the desired group $R_2$, e.g. halogen, acyloxy or hydroxy) with a reagent serving to introduce the desired group $R_2$ followed, where necessary, by removal of any protecting groups not required in the final product as described hereinafter.

In particular, where X represents a displaceable atom or group such as a halogen atom, e.g. a chlorine, bromine or iodine atom or an acyloxy group such as a hydrocarbylsulphonyloxy group, e.g. a p-toluenesulphonyloxy or a methanesulphonyloxy group, the group X may be displaced by a nucleophile serving to introduce the desired group $R_2$. The nucleophile may, for example, be an anion of general formula $R_2^\ominus$ or a molecule of general formula $R_2H$. Anions of general formula $R_2^\ominus$ may conveniently be generated by dissolving compounds of the general formula $MR_2$ (where M represents a cation such as, for example, an alkali metal ion, e.g. a sodium or potassium ion) in an appropriate solvent. Appropriate solvents include, for example, water, alcohols e.g. ethanol, ethers e.g. dioxan and tetrahydrofuran, dimethylsulphoxide and substituted amides. Reaction with nucleophilic compounds of general formula $R_2H$ may be effected optionally in a solvent such as an alcohol, e.g. ethanol or an ether, e.g. tetrahydrofuran. Such nucleophilic compounds include, for example, compounds of formula $R_aR_bNH$ such as ammonia, alkylamines and dialkylamines, e.g. ethylamine and diethylamine. This reaction is conveniently effected under elevated pressure.

Where the displaceable atom or group represented by X is a hydroxy group it will be appreciated that the compound of formula (II) may be in the enol or keto form. A hydroxy group X may be replaced by the group $R_2$ using conventional reagents. In particular a halogenating agent such as, for example, a phosphorus halide, e.g. phosphorus oxychloride, phosphorus trichloride, phosphorus pentachloride or phosphorus tribromide may be used. Suitable solvents for the reaction include hydrocarbons, e.g. toluene and halogenated hydrocarbons, e.g. chloroform and 1,2-dichloroethane.

The above reactions according to general process (A) are conveniently performed at temperatures of from $-20°$ to $150°$ C., preferably $0°$ to $100°$ C.

It will be appreciated that a number of compounds of general formula (II), e.g. those wherein X is halogen, are also compounds of the invention and such compounds may be prepared by any of general processes (A) to (E) herein. Compounds of general formula (II) where X represents an acyloxy group may be prepared by acylation of the corresponding hydroxy compound, which in turn may be made by suitable modifications of processes (B) or (C) hereinafter. For example, compounds where X represents a p-toluenesulphonyloxy group may be prepared using p-toluenesulphonyl chloride.

Where any of $R_1$, $R_3$ and $R_4$ represents a protecting group, the protecting group may be any conventional protecting group, for example as described in 'Protective Groups in Organic Chemistry' Ed. J. F. W. McOmie (Plenum Press 1973) or 'Protective Groups in Organic Synthesis' by Theodora W. Greene (John Wiley and Sons 1981). Examples of suitable protecting groups include alkyl groups such as methyl, t-butyl and methoxymethyl groups; aralkyl groups such as benzyl, diphenylmethyl, triphenylmethyl and p-methoxyphenyldiphenylmethyl groups; acyl groups, e.g. hydrocarbylcarbonyl groups of the formula RCO as discussed hereinbefore, e.g. benzoyl, pivaloyl, octanoyl and acetyl groups; and silyl groups such as trialkylsilyl groups, e.g. a t-butyldimethylsilyl group. In addition $R_3$ and $R_4$ or $R_1$ and $R_4$ may together represent a protecting group. Thus for example $R_3$ and $R_4$ may together represent an alkylidene group, e.g an isopropylidene group, or $R_1$ and $R_4$ may together represent a disiloxanyl group for example 1,1,3,3,-tetraisopropyldisilox-1,3-diyl.

According to another general process (B), compounds of the general formula (I) may be prepared by cyclising compounds of the general formula (III)

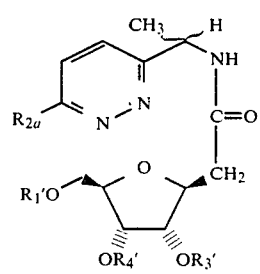

(wherein $R_1'$, $R_3'$ and $R_4'$ are protecting groups and $R_{2a}$ is as defined for $R_2$ above or represents a hydroxy group) followed, where necessary, by removal of any protecting groups not required in the final product as described hereinafter. The reaction is conveniently effected in the presence of a dehydrating agent and, optionally, a solvent. Suitable dehydrating agents include phosphorus halides such as phosphorus oxychloride, phosphorus trichloride, phosphorus pentachloride and phosphorus tribromide. Suitable solvents include hydrocarbons, e.g. toluene and halogenated hydrocarbons, e.g. chloroform and 1,2-dichloroethane. The cyclisation is conveniently effected at temperatures of from $-20°$ C. to $150°$ C., preferably of from $0°$ to $100°$ C.

It will be appreciated that in the above general process (B), where the group represented by $R_{2a}$ in formula (III) is other than $R_2$ as required in the final product an appropriate choice of reagent may be made to effect simultaneous conversion of $R_{2a}$ to $R_2$. For example, where a phosphorus halide such as phosphorus oxychloride is chosen as dehydrating agent, a hydroxy group represented by $R_{2a}$ in compounds of general formula (III) will be replaced by a halogen atom $R_2$ in the final product. By selection of an appropriate dehydrating agent one skilled in the art would have no difficulty in obtaining the desired compound of formula (I).

According to another general process (C), compounds of general formula (I) may be prepared by reacting compounds of general formula (IV)

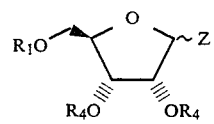

(wherein Z represents a hydroxyl group; a readily displaceable atom or group, or a group $CH_2Z_1$ in which $Z_1$ represents a readily displaceable atom or group as defined herein for Z, and $R_3$, $R_4$ and $R_1$ are as defined previously) with a compound of formula (V)

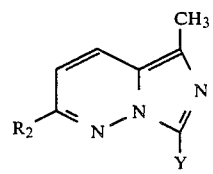

[wherein $R_2$ is as defined previously and the group Y represents a carbanion which may be a negative charge or a group of formula —e,ovs/C/ H—$Y_1$ (where $Y_1$ represents a hydrogen atom or a group capable of stabilising the carbanion, e.g. an arylsulphonyl group, which may subsequently be removed) or an ylid, for example a phosphorus ylid, such as e.g. a group of formula —CH=P(R$_6$)$_3$ (where R$_6$ represents an aryl group, e.g. a phenyl group)] followed, where necessary, by removal of any protecting groups not required in the final product as described hereinafter.

The readily displaceable atom or group represented by Z or Z$_1$ may be, for example, a halogen atom such as a chlorine, bromine or iodine atom, or an acyloxy group such as hydrocarbylcarbonyloxy, (e.g., acetoxy) or hydrocarbylsulphonyloxy, (e.g. p-toluenesulphonyloxy or methanesulphonyloxy).

The above general process (C) according to the invention is characterised by the linking of the imidazopyridazine ring to the sugar group through the intervening methylene group. It will be appreciated, therefore, that the linking methylene group may be derived from either the compound of formula (IV) or the compound of formula (V). Thus, in the above process (C), if it is desired to employ a compound of formula (IV) wherein Z represents the group CH$_2$Z$_1$, then a compound of formula (V) in which Y represents a negative charge will be employed. If it is desired to employ a compound of formula (IV) wherein Z represents a hydroxyl group then a compound of formula (V) in which Y represents a carbanion of formula —$\overline{\text{C}}$HY$_1$ (wherein Y$_1$ represents a group capable of stabilising the carbanion which may subsequently be removed) or an ylid will be employed. If it is desired to employ a compound of formula (IV) wherein Z represents a readily displaceable atom or group then a compound of formula (V) in which Y represents a carbanion of formula —$\overline{\text{C}}$H$_2$ will be employed.

The reaction is conveniently performed in solution at a temperature of from −100° to 100° C., preferably in an inert atmosphere, e.g. under argon. Suitable solvents include organic solvents such as hydrocarbons, e.g. benzene and toluene, ethers, e.g. tetrahydrofuran and dioxan, acetonitrile, N,N-disubstituted amides, e.g. dimethylformamide, and halogenated hydrocarbons, e.g. carbon tetrachloride.

The reaction including a compound of formula (V) in which Y represents a negative charge or a carbanion of formula —$\overline{\text{C}}$H$_2$ is conveniently performed at a temperature of from −100° to +100° C., e.g. −50° to +50° C.

The reaction including a compound of formula (IV) in which Z represents a hydroxyl group is conveniently performed at a temperature of from 0° to 100° C., preferably 20° to 80°.

Compounds of formula (V) may conveniently be generated in solution prior to the reaction with the compound of formula (IV), for example, from compounds of the general formula (VI)

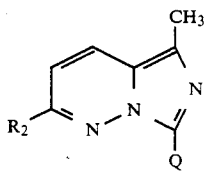
(VI)

(wherein R$_2$ is as defined previously and Q represents a hydrogen atom or the group CH$_2$X$_1$, where X$_1$ represents a readily displaceable atom or group such as a halogen atom, e.g. a chlorine, bromine or iodine atom, or a hydrocarbylsulphonyloxy group, e.g. a methanesulphonyloxy or p-toluenesulphonyloxy group). Thus, for example, compounds of formula (V) wherein Y represents a phosphorus ylid may be generated by reaction of a compound of formula (VI) wherein Q represents the group CH$_2$X$_1$ with a phosphine such as a triarylphosphine, e.g. triphenylphosphine, followed by addition of a strong base such as e.g. butyllithium. Reactions of this type are extremely well known and are described in, for example, Comprehensive Organic Chemistry, Vol. 1, Ed. J. F. Stoddart, chapter 2.2, G. H. Whittam and references therein; and N. Katagiri et al., J. Chem. Soc. Perkin. Trans. I, 1983, 201–209'. Compounds of formula (V) wherein Y represents a negative charge may be generated by reaction of the corresponding compound of formula (VI) wherein Q represents a hydrogen atom with a strong base such as an alkylmetal, e.g., butyllithium. Compounds of formula (V) wherein Y represents a carbanion of formula —$\overline{\text{C}}$H$_2$ may be generated by reaction of the corresponding compound of formula (VI) wherein Q represents the group CH$_2$X$_1$ with a metallating agent, e.g. an alkali metal such as lithium or an alkaline earth metal such as magnesium.

According to another general process (D), compounds of the general formula (I) may be prepared by acylating a compound of general formula (VII)

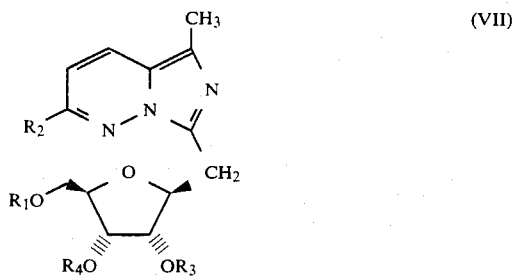
(VII)

(wherein R$_1$, R$_2$, R$_3$ and R$_4$ are as defined previously; at least one of R$_1$, R$_3$ and R$_4$ being hydrogen) with an appropriate acylating agent, e.g. with an acid of general formula (VIII)

RCOOH (VIII)

(wherein R is as defined previously) or a salt thereof, or an acylating agent corresponding thereto followed, where necessary, by removal of any protecting groups not required in the final product as described hereinafter.

It will be appreciated that when one or two of R$_1$, R$_3$ and R$_4$ is hydrogen in the desired final product, the corresponding protecting groups must be chosen to permit selective removal in the final stage. For example, R$_3$ and R$_4$ may be protected as an alkylidene residue, and R$_4$ and R$_1$ as a disiloxanyl group such as 1,1,3,3-tetraisopropyldisilox-1,3-diyl.

Acylating agents corresponding to the general formula (VIII) may include acid halides (e.g. chloride bromide, or iodide), and mixed or symmetrical anhydrides (e.g. acetic anhydride) or sulphonates (e.g. a hydrocarbylsulphonate such as p-toluenesulphonate or methanesulphonate).

Where an acid of general formula (VIII) is used, the reaction may be effected in an aqueous or non-aqueous reaction medium, optionally in the presence of a catalyst. The reaction is conveniently effected at a temperature of −50° to +100° C., e.g. 0°-50° C. Suitable solvents include hydrocarbons (e.g. benzene or toluene), halogenated hydrocarbons (e.g. dichloromethane), ethers (e.g. tetrahydrofuran or dioxan), amides (e.g. dimethylformamide), nitriles (e.g. acetonitrile), water and mixtures thereof.

If a salt of an acid of general formula (VIII) is used, it will be appreciated that an acid, e.g. a mineral acid should be added.

The acylation reaction employing an acid is conveniently effected in the presence of a coupling agent such as N-ethoxycarbonyl-2-ethoxy-1,2-dihydroquinoline or a carbodiimide, e.g. $N,N^1$-dicyclohexylcarbodiimide. The reaction may be assisted by a catalyst such as methylaminopyridine or dimethylaminopyridine. Suitable solvents include hydrocarbons, (e.g. benzene or toluene), halogenated hydrocarbons, (e.g. dichloromethane), ethers (e.g. dioxan or tetrahydrofuran), amides (e.g. dimethylformamide), esters (e.g. ethyl acetate) and nitriles, (e.g. acetonitrile). The reaction is conveniently effected at a temperature between $-50°$ and $+100°$ C., e.g. $0°-50°$ C.

Where an acid halide acylating agent is used, the reaction is conveniently effected in the presence of a base such as an organic base (e.g. a tertiary amine such as triethylamine or pyridine), and conveniently at a temperature of $-50°$ to $+150°$ C., e.g. $0°$ to $50°$ C. Suitable solvents include hydrocarbons (e.g. benzene or toluene), halogenated hydrocarbons (e.g. dichloromethane), ethers, (e.g. tetrahydrofuran or dioxan), amides (e.g. dimethylformamide), nitriles (e.g. acetonitrile) and esters (e.g. ethyl acetate). In some cases the base may act as the reaction solvent.

Where an anhydride acylating agent is used the reaction may conveniently be effected at a temperature of $-50°$ to $+100°$ C., e.g. $0°-50°$ C. Suitable solvents include hydrocarbons (e.g. benzene or toluene), halogenated hydrocarbons (e.g. dichloromethane), tertiary amines (e.g. triethylamine or pyridine), ethers (e.g. tetrahydrofuran or dioxan), amides (e.g. dimethylformamide), nitriles (e.g. acetonitrile) and esters (e.g. ethyl acetate).

Compounds of general formula (VII) may be prepared according to the methods described herein.

According to a yet further general process (E), compounds of the general formula (I) may be prepared by deprotection of compounds of the general formula (IX)

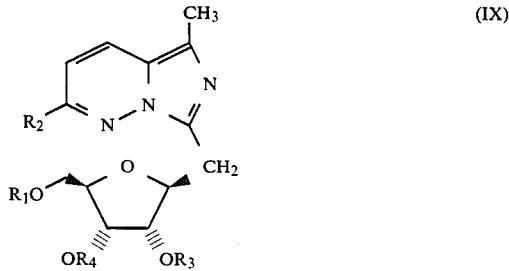

(wherein $R_1$, $R_2$, $R_3$ and $R_4$ are as defined previously, at least one of $R_1$, $R_3$ and $R_4$ representing a protecting group other than one required in the final product).

It will be appreciated that the above compounds of general formula (IX) may be formed during the general processes (A)–(D) described above and require appropriate deprotection to give compounds of general formula (I). However it will be understood that e.g. non-toxic metabolically labile esters may have been chosen as protected groups $OR_3$ and/or $OR_4$ during the preparation of compounds of formula (IX) in which case deprotection need not be effected to obtain compounds according to the invention.

Deprotection can be achieved using conventional techniques such as those described in 'Protective Groups in Organic Chemistry' Ed. J. F. W. McOmie (loc cit) and 'Protective Groups in Organic Synthesis' (loc cit). Thus, for example, an alkyl, acyl or silyl group may be removed by solvolysis, e.g. hydrolysis under acidic or basic conditions. For example where $R_3$ and $R_4$ together represent an isopropylidene group, this group may be removed by treatment with aqueous ethanolic hydrogen chloride. A benzoyl group may be removed by treatment with methanolic ammonia. An aralkyl group may be cleaved by hydrogenolysis in the presence of a noble metal catalyst, e.g. palladium on charcoal. Silyl groups e.g. as mentioned above may also conveniently be removed using a source of fluoride ions such as e.g. tetra-n-butylammonium fluoride.

It will be appreciated that where one or two of $R_1$, $R_3$ and $R_4$ in the desired final product are acyl groups, protecting groups which are to be removed should be chosen to permit selective deprotection as discussed above.

According to process (F), compounds of general formula (IX) where $R_2$ represents an amino or alkylamino group may, if desired, conveniently be alkylated in conventional manner using an alkylating agent such as an alkyl halide, e.g. methyl iodide, to obtain compounds of formula (I) where $R_2$ represents an alkylamino or dialkylamino group.

As will be appreciated, the above described processes may lead to a mixture of $\alpha$- and $\beta$-anomers which may, if desired be separated at any appropriate stage by conventional techniques such as chromatography.

The compounds of general formula (I) may, if desired, be converted into their physiological equivalents as well as into acid addition salts according to conventional methods. Thus the salts may be formed by reaction with an appropriate acid, if desired in the presence of a solvent, e.g. with hydrogen chloride in ethanol. Non-toxic metabolically labile esters may be formed by esterification using conventional techniques.

The methods indicated above for preparing the compounds of the invention can be used as the last main step in the preparative sequence. However the same general methods can be used for the introduction of the desired groups at an intermediate stage in the stepwise formation of the required compound, and it will be appreciated that these general methods can be combined in different ways in such multistage processes. The sequence of the reactions in multistage processes should of course be chosen so that the reaction conditions used do not affect the groups in the molecule which are desired in the final product.

Compounds of the general formula (III) may be prepared by acylation of compounds of the general formula (X)

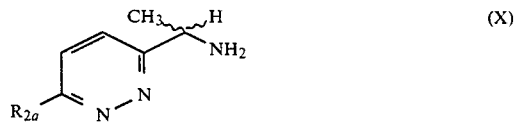

(wherein $R_{2a}$ is as defined previously) with an acid of formula (XI)

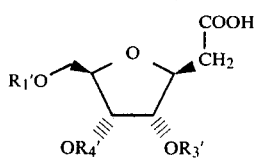

(wherein $R_1'$, $R_3'$ and $R_4'$ are as defined previously) or with an acylating agent corresponding thereto such as, for example, a lactone of formula (XII)

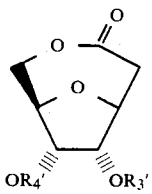

(wherein $R_3'$ and $R_4'$ are as defined previously). Where an acid of formula (XI) is reacted with an amine of formula (X), the reaction is conveniently effected in the presence of a coupling agent such as N-ethoxycarbonyl-2-ethoxy-1,2-dihydroquinoline or a carbodiimide, e.g. N,N'-dicyclohexylcarbodiimide.

Compounds of the general formula (X) wherein $R_{2a}$ is as defined for $R_2$ may be prepared from compounds of the general formula (XIII)

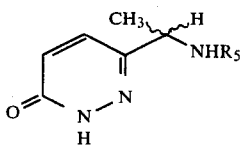

(wherein $R_5$ represents a hydrogen atom or a protecting group, such as an acyl group, e.g. an acetyl or benzoyl group) by methods analogous to those used in general process (A) for the preparation of compounds of general formula (I) from compounds of general formula (II) where X represents a hydroxy group, and followed where necessary by removal of a protecting group $R_5$ as described hereinafter.

Compounds of the general formula (XIII) may be prepared by the processes described in British Patent Specification No. 1,583,911.

Compounds of the general formula (XI) may be prepared by reaction of compounds of general formula (XIV)

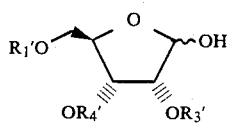

(wherein $R_1'$, $R_3'$ and $R_4'$ are as defined previously) with a phosphorus ylid of formula (XV)

$Y_2$=CHCOOR$_7$     (XV)

(wherein the group $Y_2$=CH— represents a phosphorus ylid group e.g. as exemplified previously and $R_7$ represents a carboxyl blocking group, for example a benzyl group) followed by the removal of the carboxyl blocking group represented by $R_7$. Alternatively a phosphorus ylid of formula (XVI)

$Y_2$=CHCN     (XVI)

(wherein $Y_2$=CH is as defined previously) may be used, followed by hydrolysis of the nitrile group. For examples illustrating reactions of this type see H. Ohrui et al, J. Org. Chem, 1977, 42, 1951–57 and J. Am. Chem. Soc., 1975, 97, 4602–4613. It will be appreciated that in certain cases, it may not be necessary to remove the carboxyl blocking group $R_7$ before reaction with the compound of formula (X). Thus the protected intermediate may be an acylating agent corresponding to the compound of formula (XI) and may be used directly to prepare compounds of the general formula (III).

Compounds of general formula (VI) may be prepared by reacting compounds of general formula (X) with compounds of general formula (XVII)

QCOOH     (XVII)

(wherein Q is as defined previously) using the method described for the preparation of compounds of general formula (III), followed by cyclisation of the intermediate amide using methods described in general process (B).

Compounds of the general formulae (IV) and (XIV) may be prepared by conventional methods from ribose.

Many of the intermediates defined above are believed to be novel per se and form further aspects of our invention, e.g. compounds of formula (II) wherein X is hydroxy or acyloxy; and compounds of formula (III).

The following non-limiting Examples serve to illustrate the present invention:

INTERMEDIATE 1

Benzyl 3,6-anhydro-2-deoxy-4,5-O-isopropylidene-D-alloheptonate

Benzyloxycarbonylmethylenetriphenylphosphorane (18 g) [Chopard, P. A., Helv. Chim. Acta., 1967, Vol. 50, p1016] and 2,3-O-isopropylidene-D-ribose (6.28 g) were dissolved in acetonitrile (100 ml) and the solution was heated at reflux for 3 h. The solvent was removed in vacuo and the residual oil was purified by column chromatography on silica gel. Elution with diethyl ether/cyclohexane (4:1) afforded the title compound (8.2 g).

$\nu$max (CHBr$_3$); 3590, 3480 and 1730 cm$^{-1}$.

INTERMEDIATE 2

Benzyl 3,6-anhydro-7-O-benzoyl-2-deoxy-4,5-O-isopropylidene-D-alloheptonate

Intermediate 1 (7.0 g) was dissolved in dichloromethane (70 ml) and added to a solution of benzoic acid (2.8 g), dicyclohexylcarbodiimide (4.92 g) and 4-dimethylaminopyridine (260 mg) in dichloromethane (150 ml). Stirring was maintained for 18 h at room temperature under a nitrogen atmosphere. The reaction mixture was filtered and the solvent was removed in vacuo. The residue was purified by column chromatography on silica gel; elution with petrol/ethyl acetate (4:1) provided the title compound (9.1 g).

$\nu$max (CHBr$_3$); 1720, 1370, 1270 and 1070 cm$^{-1}$.

INTERMEDIATE 3

3,6-Anhydro-7-O-benzoyl-2-deoxy-4,5-O-isopropylidene-D-alloheptonic acid

Intermediate 2 (8.7 g) was dissolved in ethyl acetate (200 ml) and added to a pre-reduced suspension of 10% PdO on carbon (600 mg) in ethyl acetate (100 ml). The solution was hydrogenated for 22 h at atmospheric pressure, filtered through 'Hyflo' and the filtrate was evaporated in vacuo to a gum which was dissolved in diethyl ether (300 ml). The solution was base extracted with saturated sodium bicarbonate solution (3×200 ml) followed by neutralisation of the combined basic extracts to pH 3 with 5N hydrochloric acid. Further extraction with ethyl acetate (3×250 ml), drying (MgSO$_4$) and decolourisation (charcoal) provided a solution of the acid which was evaporated in vacuo to a solid gum (68 g).

$\nu$max (CHBr$_3$); 3490, 1745, 1710 and 1370 cm$^{-1}$.

INTERMEDIATE 4

3,6-Anhydro-7-O-benzoyl-2-deoxy-4,5-O-isopropylidene-D-alloheptonic acid, N-1-(1,6-dihydro-6-oxo-pyridazin-3-yl)ethylamide Intermediate 3 (9.4 g) was dissolved in dichloromethane (200 ml) and added to a solution of 1-(2,3-dihydro-3-oxo-pyridazin-6-yl)ethylamine (4.9 g) [prepared as described in British Patent Specification No. 1,583,911] in dichloromethane (100 ml). The mixture was stirred for 30 min before dicyclohexylcarbodiimide (5.95 g) was added and stirring was continued for 60 h. The reaction mixture was filtered and evaporated in vacuo to give a residue which was purified by column chromatography on silica gel. Elution with ethyl acetate/ethanol (20:1) afforded the title compound as a white solid (9.5 g).

$\nu$max (CHBr$_3$); 3370, 1715, 1675, 1650, 1512 and 1378 cm$^{-1}$.

EXAMPLE 1

7-(5'-O-Benzoyl-2',3'-O-isopropylidene-$\beta$-D-ribofuranosylmethyl)-2-chloro-5-methylimidazo[1,5-b]pyridazine Intermediate 4 (9.1 g) was dissolved in 1,2-dichloroethane (300 ml) and phosphoryl chloride (8.5 ml) was added with stirring. The solution was heated at reflux for 3.3 h, cooled and evaporated in vacuo. The resultant residue was treated with saturated sodium bicarbonate solution (400 ml) and extracted with ethyl acetate (4×200 ml) with vigorous shaking. The combined extracts were dried (MgSO$_4$) and evaporated in vacuo; the residue (6.2 g) was purified by column chromatography on silica gel. Elution with ethyl acetate/cyclohexane (7:3) afforded the title compound (4.63 g) as a yellow foam.

$\tau$(250 MHz, CDCl$_3$) 1.93–2.6 (6H, m, Ar—H and H-4), 3.63 (1H, d, H-3), 5.21 (1H, dd, H-2'), 5.29 (1H, dd, H-3'), 5.39 (1H, dt, H-1'), 5.56 (1H, dd, H-5'$_a$), 5.56 (2H, m, H-4' and H-5'$_b$), 6.5–6.7 (2H, ABX, rib—CH$_2$), 7.54 (3H, s, 5—CH$_3$), 8.46 (3H, s, isopropylidene CH$_3$), 8.64 (3H, s, isopropylidene-CH$_3$); $\nu$max (CHBr$_3$) 1715 cm$^{-1}$.

EXAMPLE 2

7-(5'-O-Benzoyl-$\beta$-D-ribofuranosylmethyl)-2-chloro-5-methylimidazo[1,5-b]pyridazine The product of Example 1 (3.5 g) was dissolved in ethanol (140 ml) and 0.6N hydrochloric acid solution (100 ml) was added. The yellow solution was heated at 80° C. for 1 h, basified (to pH 9) with sodium carbonate solution and concentrated in vacuo (to remove ethanol). The resultant aqueous suspension was extracted with ethyl acetate (3×200 ml) and the combined extracts were dried (MgSO$_4$). Evaporation in vacuo gave the title compound as a solid (3.20 g), m.p. 155°–157° C.

$\nu$max (CHBr$_3$); 3580, 3500 and 1710 cm$^{-1}$.

EXAMPLE 3

2-Chloro-5-methyl-7-($\beta$-D-ribofuranosylmethyl)imidazo[1,5-b]pyridazine

The product of Example 2 (4.5 g) was added to methanol (1000 ml) which had been presaturated with ammonia. The mixture was stirred for 15 min. and stood for 2 days at room temperature. The solvent was evaporated under reduced pressure and the residue was purified by recrystallization from ethyl acetate to afford the title compound (3.1 g) as a solid m.p. 171°–174°, $\tau$ (100 MHz, DMSO-d$_6$) 1.77 (1H, d, H-4), 3.29 (1H, d, H-3), 4.9–5.4 (3H, m, OH), 5.55–6.95 (8H, m, H-1', H-2', H-3', H-4', 2H-5', homo-CH$_2$), 7.56 (3H, s, Ar—CH$_3$).

EXAMPLE 4

7-(2',3'-O-Isopropylidene-$\beta$-D-ribofuranosylmethyl)-5-methyl-2-(methylamino)-imidazo[1,5-b]pyridazine The product of Example 1 (1.3 g) was dissolved in 33% ethanolic methylamine (120 ml) and the solution was placed in a pressure vessel of 250 ml capacity. The vessel was heated on a steam-bath for 7.5 h and allowed to cool to room temperature. The solvent was removed under reduced pressure and the residue was purified by column chromatography on silica gel. Elution with dichloromethane:methanol (9:1) afforded the title compound (900 mg) as a foam. $\tau$ (200 MHz, CDCl$_3$) 2.7 (1H, d, H-4), 4.17 (1H, d, H-3), 5.19 (1H, m, H-3'), 5.39 (1H, m, H-2'), 5.43–5.6 (2H, m, NH+H-1'), 5.82 (1H, m, H-4'), 6.16, 6.36 (2H, dd, 2H-5'), 6.67 (2H, m, homo-CH$_2$), 7.11 (3H, d, N—CH$_3$), 7.67 (3H, s, Ar—CH$_3$), 8.49 (3H, s, isopropylidene—CH$_3$), 8.70 (3H, s, isopropylidene—CH$_3$). $\nu_{max}$. (CHBr$_3$) 3465, 3160, 1636, 1073 cm$^{-1}$.

EXAMPLE 5

5-Methyl-2-methylamino-7-($\beta$-D-ribofuranosylmethyl)imidazo[1,5-b]pyridazine Method (i)

The product of Example 3 (520 mg) was dissolved in 33% ethanolic methylamine (100 ml) and the solution was placed in a pressure vessel of 250 ml capacity. The vessel was heated on a steam-bath for 8 h and allowed to cool to room temperature. The solvent was removed under reduced pressure and the residue was purified by column chromatography on silica gel using dichloromethane:methanol (4:1) for elution. Further purification by crystallization from methanol gave the title compound (270 mg) as crystals m.p. 238°–242°. $\tau$ (200 MHz, DMSO-d$_6$) 2.39 (1H, d, H-4), 3.20 (1H, m, N-H), 3.91 (1H, d, H-3), 4.80–5.39 (3H, m, OH), 5.85 (1H, m, H-1'), 6.01–6.20 (2H, m, H-2'+H-3'), 6.32 (1H, m, H-4'), 6.47–6.61 (2H, m, 2H-5'), 6.92 (2H, m, homo—CH$_2$), 7.20 (3H, d, N—CH$_3$), 7.72 (3H, s, Ar—CH$_3$).

Method (ii)

The product of Example 4 (100 mg) was dissolved in ethanol (3 ml) and 0.6N-HCl (1.5 ml) was added. The mixture was stirred at 70° for 1 h and cooled to room temperature. The mixture was basified by the addition of solid sodium carbonate and the solvent was removed under reduced pressure. The residue was azeotroped with toluene and the product was then extracted into hot methanol (20 ml). On cooling the methanolic solution, crystals of the title compound (62 mg) were obtained having similar spectral characteristics to those described above.

EXAMPLE 6a 7-(5'-O-Benzoyl-2',3'-O-isopropylidene-β-D-ribofuranosylmethyl)-5-methyl-2-(methylamino)imidazo[1,5-b]pyridazine The product of Example 4 (500 mg) in dichloromethane (10 ml) was added to a suspension of benzoic acid (180 mg), dicyclohexylcarbodiimide (310 mg) and 4-dimethylaminopyridine (22 mg) in dichloromethane (6 ml).

The mixture was stirred at room temperature for 20 h, filtered and the filtrate was evaporated to dryness under reduced pressure. Purification of the residue by column chromatography on silica gel using dichloromethane:methanol (20:1) for elution afforded the title compound (520 mg) as a foam. $\nu_{max}$ (CHBr$_3$) 3465, 1720, 1633, 1273, 1072 cm$^{-1}$.

By the same method the following compounds were prepared.

(b) 2-Chloro-7-(2',3'-O-isopropylidene-5'-O-phenylacetyl-β-D-ribofuranosylmethyl)-5-methylimidazo[1,5-b]pyridazine $\nu_{max}$ (CHBr$_3$) 1735, 1615 cm$^{-1}$.

(c) 2-Chloro-7-(5'-O-hexanoyl-2',3'-O-isopropylidene-β-D-ribofuranosylmethyl)-5-methylimidazo[1,5-b]pyridazine $\nu_{max}$ (CHBR$_3$) 1730, 1614 cm$^{-1}$.

(d) 7-(5'-O-Butylanoyl-2',3'-O-isopropylidene-β-D-ribofuranosylmethyl)-2-chloro-5-methylimidazo[1,5-b]pyridazine $\nu_{max}$ (CHBr$_3$) 1730, 1615, 1075 cm$^{-1}$.

(e) 2-Chloro-[5'-O-(2,2-dimethylpropanoyl)-2',3'-O-isopropylidene-β-D-ribofuranosylmethyl]-5-methylimidazo[1,5-b]pyridazine $\nu_{max}$ (CHBr$_3$) 1720, 1611, 1072 cm$^{-1}$.

(f) 2-Chloro-7-[5'-O-(cyclohexanecarbonyl)-2',3'-O-isopropylidene-β-D-ribofuranosylmethyl]-5-methylimidazo[1,5-b]pyridazine $\nu_{max}$ (CHBr$_3$) 1730, 1615, 1535 cm$^{-1}$.

(g) 7-[5'-O-(1-Adamantanecarbonyl)-2',3'-O-isopropylidene-β-D-ribofuranosylmethyl]-2-chloro-5-methylimidazo[1,5-b]pyridazine $\nu_{max}$ (CHBr$_3$) 1720, 1611, 1070 cm$^{-1}$.

(h) 2-Chloro-7-[2',3'-O-isopropylidene-5'-O-(2-naphthoyl)-β-D-ribofuranosylmethyl]-5-methylimidazo[1,5-b]-pyridazine $\nu_{max}$ (CHBr$_3$) 1713, 1615 cm$^{-1}$.

(i) 7-(5'-O-Benzoyl-2',3'-O-isopropylidene-β-D-ribofuranosylmethyl)-2-(dimethylamino)-5-methylimidazo[1,5-b]pyridazine τ (60 MHz, CDCl$_3$) 7.07 (s, 6H; N(CH$_3$)$_2$), 7.67 (s, 3H; Ar—CH$_3$), 8.50 and 8.71 (s, 3H; C(CH$_3$)$_2$).

(j) 7-(5'-O-Benzoyl-2',3'-O-isopropylidene-β-D-ribofuranosylmethyl)-5-methyl-2-(N-pentylamino)imidazo[1,5-b]pyridazine τ (60 MHz, CDCl$_3$) 1.75–2.72 (m, 5H; PhCO), 7.63 (s, 3H; Ar—CH$_3$), 8.46 and 8.67 (s, 3H; C(CH$_3$)$_2$.

(k) 7-(5'-O-Benzoyl-2'-3'-O-isopropylidene-β-D-ribofuranosylmethyl)-5-methyl-2-piperidinoimidazo[1,5-b]pyridazine τ (250 MHz; CDCl$_3$) 2.56 (d, 1H; H-4) 3.70 (d, 1H; H-3) 7.54 (s, 3H; ArCH$_3$) 8.42 and 8.62 (s, 3H; C(CH$_3$)$_2$); $\nu_{max}$ (CHBr$_3$) 1715 cm$^{-1}$.

(l) 2-Chloro-7-(2',3'-O-isopropylidene-5'-O-octanoyl-β-D-ribofuranosylmethyl)-5-methylimidazo[1,5-b]pyridazine $\nu_{max}$ 1732, 1615 cm$^{-1}$, τ (250 MHz; CDCl$_3$) 7.56 (s, 3H; Ar—CH$_3$) 8.53 and 8.72 (s, 3H; C(CH$_3$)$_2$).

(m) 2-Chloro-7-(5'-O-decanoyl-2',3'-O-isopropylidene-β-D-ribofuranosylmethyl)-5-methylimidazo[1,5-b]pyridazine $\nu_{max}$ (CHBr$_3$) 1730, 1613, 1073 cm$^{-1}$; τ (250 MHz; CDCl$_3$) 7.54 (s, 3H; Ar-CH$_3$) 8.50 and 8.69 (s, 3H; C(CH$_3$)$_2$).

The following Table I is a summary of the reaction conditions used to prepare the products of Examples (6b) to (6h). In the Table, the following abbreviations are used:

DCC—dicyclohexylcarbodiimide
DMAP—4-dimethylaminopyridine

The group R$^2$ in the alcohol starting material is defined by reference to the formula below.

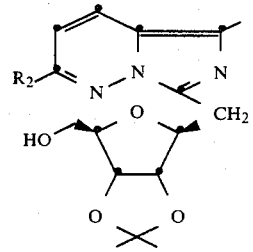

TABLE I

| Ex No. | Acid | R$_2$ | Wt of Alcohol (mg) | Amount of Acid | Wt of DCC (mg) | Wt of DMAP (mg) | Vol of Solvent (ml) | Reaction Time | Yield (mg) |
|---|---|---|---|---|---|---|---|---|---|
| 6b | phenylacetic | Cl | 300 | 130 mg | 200 | 10 | 10 + 3 | 20h | 282 |
| 6c | 1-hexanoic | Cl | 300 | 0.12 ml | 200 | 10 | 8 + 3 | 22h | 380 |
| 6d | 1-butanoic | Cl | 400 | 0.12 ml | 270 | 15 | 8 + 3 | 20h | 395 |
| 6e* | 2,2-dimethyl-propanoic | Cl | 400 | 122 mg | 250 | 12 | 8 + 3 | 10 days | 282 |
| 6f | cyclohexane-carboxylic | Cl | 400 | 155 mg | 250 | 10 | 8 + 3 | 3 days | 510 |
| 6g | 1-adamantane-carboxylic | Cl | 396 | 227 mg | 272 | 15 | 8 + 3 | 7 days | 326 |
| 6h | 2-naphthoic | Cl | 401 | 217 mg | 276 | 15 | 8 + 3 | 2 days | 482 |
| 6i | benzoic | N(CH$_3$)$_2$ | 180 | 76 mg | 126 | 10 | 7 + 3 | 22h | 182 |
| 6j | benzoic | N(CH$_2$)$_4$CH$_3$ | 300 | 129 mg | 213 | 19 | 10 + 4 | 20h | 342 |
| 6k | benzoic |  | 402 | 141 mg | 242 | 12 | 10 + 3 | 48h | 407 |

TABLE I-continued

| Ex No. | Acid | R$_2$ | Wt of Alcohol (mg) | Amount of Acid | Wt of DCC (mg) | Wt of DMAP (mg) | Vol of Solvent (ml) | Reaction Time | Yield (mg) |
|---|---|---|---|---|---|---|---|---|---|
| 6l | 1-octanoic | Cl | 403 | 0.2 ml | 270 | 15 | 8 + 3 | 20h | 670 |
| 6m | 1-decanoic | Cl | 380 | 206 mg | 312 | 12 | 7 + 3 | 20h | 550 |

*A further 150 mg of 2,2-dimethylpropanoic acid and 320 mg of dicyclohexylcarbodiimide were added after 3 days.

EXAMPLE 7a 7-(5'-O-Benzoyl-β-D-ribofuranosylmethyl)-5-methyl-2-(methylamino)imidazo[1,5-b]pyridazine A solution of the product of Example 6(a) (500 mg) in ethanol (15 ml) was treated with 0.6N-HCl (7.5 ml) and the mixture was stirred at 75° for 45 min and cooled to room temperature. The mixture was basified by the addition of solid sodium carbonate and the ethanol removed under reduced pressure. The residue was diluted with water and the product isolated by repeated extraction into ethyl acetate. Crystallisation from ethyl acetate gave the title product (360 mg) as a solid m.p. 163°–165°. $\nu_{max}$ (nujol) 3360, 3200–2500, 1713, 1632, 1276 cm$^{-1}$.

By the same method the following compounds were prepared.

(b) 2-Chloro-5-methyl-7-(5'-O-phenylacetyl-β-D-ribofuranosylmethyl)imidazo[1,5-b]pyridazine m.p. 112°, $\nu_{max}$ (nujol) 3505, 3110, 1725, 1613 cm$^{-1}$.

(c) 2-Chloro-7-(5'-O-hexanoyl-β-D-ribofuranosylmethyl)-5-methylimidazo[1,5-b]pyridazine m.p. 99°–100°, $\nu_{max}$ (nujol) 3482, 3150, 1720, 1615 cm$^{-1}$.

(d) 7-(5'-O-Butanoyl-β-D-ribofuranosylmethyl)-2-chloro-5-methylimidazo[1-5-b]pyridazine m.p. 83°–84°, $\nu_{max}$ (nujol) 3480, 3150, 1720, 1615 cm$^{-1}$.

(e) 2-Chloro-7-[5'-O-(2,2-dimethylpropanoyl)-β-D-ribofuranosylmethyl]-5-methylimidazo[1,5-b]pyridazine m.p. 126°–127° C., $\nu_{max}$ (nujol) 3350, 3400–2500, 1720, 1618 cm$^{-1}$.

(f) 2-Chloro-7-[5'-O-(cyclohexanecarbonyl)-β-D-ribofuranosylmethyl]-5-methylimidazo[1,5-b]pyridazine m.p. 106°–108°, $\nu_{max}$ (nujol) 1733, 1717, 1615, 1532 cm$^{-1}$.

(g) 7-[5'-O-(1-Adamantanecarbonyl)-β-D-ribofuranosylmethyl]-2-chloro-5-methylimidazo[1,5-b]pyridazine m.p. 159°–160° C., $\nu_{max}$ (nujol) 3600–2500, 1722, 1618 cm$^{-1}$.

(h) 2-Chloro-7-[5'-O-(2-naphthoyl)-β-D-ribofuranosylmethyl]-5-methylimidazo[1,5-b]pyridazine m.p. 144°–145°, $\nu_{max}$ (nujol) 1722, 1620 cm$^{-1}$.

(i) 7-(5'-O-Benzoyl-β-D-ribofuranosylmethyl)-2-(dimethylamino)-5-methylimidazo[1,5-b]pyridazine m.p. 165°–166°, $\nu_{max}$ (nujol) 3502, 3160, 1708, 1638, 1578 cm$^{-1}$.

(j) 7-(5'-O-Benzoyl-β-D-ribofuranosylmethyl)-5-methyl-2-(N-pentylamino)imidazo[1,5-b]pyridazine m.p. 111°–112° τ (200 MHz; DMSO-d6) 2.42 (d, 1H; H-4) 3.90 (d, 1H; H-3) 7.73 (s, 3H; Ar—CH$_3$) $\nu_{max}$ (nujol) 1722 cm$^{-1}$.

(k) 7-(5'-O-Acetyl-β-D-ribofuranosylmethyl)-2-chloro-5-methylimidazo[1,5-b]pyridazine m.p. 134°–135°, $\nu_{max}$ (nujol) 3525, 3300–2500, 1719, 1615 cm$^{-1}$.

(l) 7-(5'-O-Benzoyl-β-D-ribofuranosylmethyl)-2-bromo-5-methylimidazo[1,5-b]pyridazine m.p. 162°–164° $\nu_{max}$ (nujol) 3510–2470, 1695 cm$^{-1}$.

(m) 2-Chloro-7-(5'-O-octanoyl-β-D-ribofuranosylmethyl)-5-methylimidazo[1,5-b]pyridazine m.p. 95°; $\nu_{max}$ (nujol) 1721, 1615, 1532 cm$^{-1}$; τ 200 MHz; DMSO-d$_6$) 1.87 (d, 1H; H-4), 3.38 (d, 1H, H-3), 7.58 (s, 3H; Ar—CH$_3$) 7.71 (t, 2H; —CH$_2$CO$_2$—).

(n) 2-Chloro-7-(5'-O-decanoyl-β-D-ribofuranosylmethyl)-5-methyl-imidazo[1,5-b]pyridazine, hydrochloride m.p. 122°–123°; $\nu_{max}$ (nujol) 1742, 1650, 1572 cm$^{-1}$; τ (250 MHz; DMSO-d$_6$) 1.49 (d, 1H; H-4), 2.88 (d, 1H; H-3), 7.40 (s, 3H; Ar—CH$_3$), 7.71 (t, 2H; —CH$_2$CO$_2$—).

The following Table II is a summary of the reaction conditions used to prepare the products of Examples 7(b) to 7(n). The groups R$_1$ and R$_2$ in the starting material are defined by reference to the formula below.

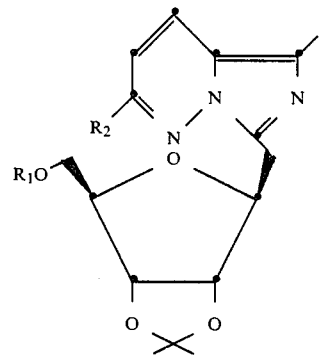

TABLE II

| Ex. No. | R$_1$ | R$_2$ | Wt. of compd. (mg) | Vol. of solvent (ml) | Volume of 0.6 NHCl (ml) | Reaction Temp. (°C.) | Reaction Time | Crystallisation Solvent | Yield (mg) |
|---|---|---|---|---|---|---|---|---|---|
| 7b* | ⟨phenyl⟩—CH$_2$CO | Cl | 210 | 15 | 7.5 | 40 | 3h | ethyl acetate | 56 |
| 7c* | CH$_3$(CH$_2$)$_4$CO | Cl | 320 | 15 | 7.5 | 45 | 4h | diethyl ether | 119 |
| 7d* | CH$_3$(CH$_2$)$_2$CO | Cl | 330 | 20 | 10 | 50 | 2h | diethyl ether | 183 |
| 7e* | (CH$_3$)$_3$CCO | Cl | 230 | 20 | 10 | 80 | 0.75h | diethyl ether | 191 |

TABLE II-continued

| Ex. No. | R₁ | R₂ | Wt. of compd. (mg) | Vol. of solvent (ml) | Volume of 0.6 NHCl (ml) | Reaction Temp. (°C.) | Reaction Time | Crystallisation Solvent | Yield (mg) |
|---|---|---|---|---|---|---|---|---|---|
| 7f* | cyclohexyl-CO | Cl | 440 | 20 | 10 | 50 | 2h | diethyl ether | 192 |
| 7g* | adamantyl-CO | Cl | 273 | 20 | 10 | 80 | 1h | diethyl ether | 225 |
| 7h | naphthyl-CO | Cl | 420 | 18 | 9 | 80 | 0.75h | diethyl ether followed by ethyl acetate | 375 |
| 7i | phenyl-CO | N(CH₃)₂ | 178 | 10 | 5 | 60 | 2h | diethyl ether | 156 |
| 7j | phenyl-CO | N(CH₂)₄CH₃ | 340 | 8 | 4 | 80 | 1h | diethyl ether | 187 |
| 7k* | CH₃CO | Cl | 495 | 20 | 10 | 40 | 4h | ethyl acetate | 166 |
| 7l | phenyl-CO | Br | 120 | 5 | 2.5 | 75 | 1.2h | diethyl acetate | 89 |
| 7m | CH₃(CH₂)₆CO | Cl | 560 | 20 | 10 | 50 | 2h | ethyl acetate | 186 |
| 7n* | CH₃(CH₂)₈CO | Cl | 440 | 10 | 5 | 60 | 2h | ** | 215 |

*The compound was purified by chromatography on silica gel eluting with dichloromethane: methanol (9:1) prior to crystallisation.
**The product was taken up in dichloromethane and treated with ethanolic HCl followed by diethyl ether.

EXAMPLE 8

2-Chloro-7-(2′,3′-O-isopropylidene-β-D-ribofuranosylmethyl)-5-methylimidazo[1,5-b]pyridazine The product of Example 1 (8 g) was added to methanol (1200 ml) which had been presaturated with ammonia. The mixture was shaken and stood for 48 h at room temperature in a stoppered flask. The solvent was evaporated under reduced pressure and the residue was purified by column chromatography on silica gel using ethyl acetate for elution to afford the title product (5.6 g) as a foam. $v_{max}$ (CHBr₃) 3235, 1619, 1073 cm⁻¹.

EXAMPLE 9

7-(5′-O-Acetyl-2′,3′-O-isopropylidene-β-D-ribofuranosylmethyl)-2-chloro-5-methylimidazo[1,5-b]pyridazine The product of Example 8 (520 mg) was added to a mixture of acetic anhydride (5 ml) and pyridine (5 ml). The resulting mixture was stirred at room temperature for 2.5 h and evaporated under reduced pressure. The residue was co-evaporated with methanol and then taken up in ethyl acetate. The solution was washed with brine, dried and the solvent was removed under reduced pressure to afford the title compound (570 mg) as a syrup. $v_{max}$ (CHBr₃) 1736, 1615 cm⁻¹.

EXAMPLE 10

7-(5′-O-Benzoyl-2′,3′-O-isopropylidene-β-D-ribofuranosylmethyl)-2-bromo-5-methylimidazo[1,5-b]pyridazine A solution of Intermediate 4 (502 mg) and phosphoryl bromide (1.61 g) in 1,2-dichloroethane (20 ml) was stirred and refluxed for 2 h and the solvent was removed under reduced pressure. The residue was taken up in ethyl acetate and the solution was washed with aqueous sodium bicarbonate. The solvent was removed under reduced pressure and the residue was purified by chromatography on silica gel. Elution with ethyl acetate afforded the title compound (131 g) as a viscous oil $v_{max}$ (CHBr₃) 1715, 1610, 1270 cm⁻¹.

EXAMPLE 11

2-(Dimethylamino)-5-methyl-7-(β-D-ribofuranosylmethyl)imidazo[1,5-b]pyridazine

The product of Example 3 (520 mg) was treated with a 33% solution of dimethylamine in ethanol (100 ml) and the resulting solution was stored in a closed vessel for 4 days at room temperature. The mixture was evaporated to dryness under reduced pressure and the residue was again treated with ethanolic dimethylamine (100 ml) for 7 days at room temperature. The mixture was evaporated to dryness under reduced pressure and the residue was purified by chromatography on silica gel. Elution with dichloromethane:methanol (4:1) and subsequent recrystallization of the product from methanol afforded the title compound (320 mg) as needles m.p. 231°–232° $\nu_{max}$(nujol) 3470, 3140, 1640, 1631, 1578 cm$^{-1}$.

EXAMPLE 12

2-(Dimethylamino)-7-(2′,3′-O-isopropylidene-β-D-ribofuranosylmethyl)-5-methylimidazo[1,5-b]pyridazine The product of Example 11 (164 mg) in acetone (8 ml) and 2,2-dimethoxypropane (4 ml) was treated with toluene-4-sulphonic acid (20 mg) and the mixture was stirred for 46 h at room temperature. 0.6N-HCl (10 ml) was added, the mixture was stirred for 1 min and basified by the addition of sodium bicarbonate. The product was extracted into ethyl acetate and removal of the solvent afforded the title compound (180 mg) as a foam τ (60 MHz, CDCl$_3$) 7.0 (s, 6H; N(CH$_3$)$_2$) 7.65 (s, 3H; Ar—CH$_3$) 8.48 and 8.70 (s, 3H; C(CH$_3$)$_2$).

EXAMPLE 13

5-Methyl-2-(N-octylamino)-7-(β-D-ribofuranosylmethyl)imidazo[1,5-b]pyridazine

The product of Example 2 (617 mg) was dissolved in 1-octylamine (14 ml). The solution was stirred at 110° C. for 5 h and partitioned between ethyl acetate and brine. The organic phase was separated, dried and the solvent removed under reduced pressure to afford a viscous oil which was purified by chromatography on silica gel using dichloromethane:methanol (9:1) for elution. The resulting gum was further purified by crystallization from ether to afford the title compound (151 mg) as crytals m.p. 105°–106° τ (250 MHz, CDCl$_3$) 2.65 (d, 1H; H-4) 4.12 (d, 1H; H-3) 6.69 (dt, 2H; —CH$_2$—NH) 7.66 (s, 3H; Ar—CH$_3$).

EXAMPLE 14

5-Methyl-2-(N-methyl-N-octylamino)-7-(β-D-ribofuranosylmethyl)imidazo[1,5-b]pyridazine and 7-(5′-O-Benzoyl-β-D-ribofuranosylmethyl)-5-methyl-2-(N-methyl-N-octylamino)imidazo[1,5-b]pyridazine The product of Example 2 (532 mg) was dissolved in N-methyloctylamine (10 ml) and the solution was stirred at 110° for 60 h. The mixture was taken up in ethyl acetate and the solution was washed with brine and dried. Removal of the solvent under reduced pressure afforded a viscous oil which was subjected to chromatography on silica gel using dichloromethane:methanol (19:1) for elution. Such treatment afforded two products which were each further purified by trituration with light petroleum. The more polar product, the first-named title compound (151 mg) was obtained as a solid m.p. 66°–67° τ (250 MHz, DMSO-d$_6$) 2.21 (d, 1H; H-4) 3.46 (d, 1H; H-3) 6.95 (s, 3H; N—CH$_3$) 7.66 (s, 3H; Ar—CH$_3$). The less polar product, the second-named title compound (52 mg) was obtained as solid m.p. 71°–72° τ (250 MHz, DMSO-d$_6$) 2.25 (d, 1H; H-4) 3.52 (d, 1H; H-3) 7.01 (s, 3H; N—CH$_3$) 7.68 (s, 3H; Ar—CH$_3$) $\nu_{max}$ (nujol) 1708 cm$^{-1}$.

EXAMPLE 15

5-Methyl-2-(N-pentylamino)-7-(β-D-ribofuranosylmethyl)imidazo[1,5-b]pyridazine

The product of Example 2 (633 mg) was dissolved in 1-pentylamine (10 ml) and the solution was stirred and refluxed for 24 h. The mixture was concentrated under reduced pressure to a gum which was purified by chromatography on silica gel using dichloromethane:methanol (9:1) for elution. Subsequent recrystallization of the product from dichloromethane afforded the title compound (207 mg) as a solid m.p. 133° (decomp.) τ (200 MHz, DMSO-d$_6$) 2.39 (d, 1H; H-4) 3.87 (d, 1H; H-3) 6.78 (m, 2H; —CH$_2$NH—) 7.73 (s, 3H; Ar—CH$_3$).

EXAMPLE 16

7-(2′,3′-O-Isopropylidene-β-D-ribofuranosylmethyl)-5-methyl-2-(N-pentylamino)imidazo[1,5-b]pyridazine The product of Example 15 (280 mg) and toluene-4-sulphonic acid (158 mg) were dissolved in a mixture of acetone (12 ml) and 2,2-dimethoxypropane (6 ml) and the resulting solution was stirred at room temperature for 20 h. 1M-HCl (20 ml) was added, the solution was stirred for 30 seconds and made alkaline by the addition of sodium bicarbonate solution. The product was extracted into ethyl acetate and the extracts were dried. Removal of the solvent under reduced pressure afforded the title compound (300 mg) as a foam τ (60 MHz, CDCl$_3$) 7.70 (s, 3H; Ar—CH$_3$) 8.48 and 8.68 (s, 3H; C(CH$_3$)$_2$).

EXAMPLE 17

7-(2′,3′-O-Isopropylidene-β-D-ribofuranosylmethyl)-5-methyl-2-piperidinoimidazo[1,5-b]pyridazine A solution of the product of Example 8 (980 mg) in piperidine (20 ml) was heated under reflux with stirring for 3 h. Excess reagent was removed under reduced pressure and the residue was partitioned between water and ethyl acetate. The organic phase was washed with brine, dried and the solvent removed under reduced pressure to afford the title compound (1.08 g) as a foam. τ (250 MHz; CDCl$_3$) 2.57 (d, 1H; H-4) 3.70 (d, 1H; H-3) 7.62 (s, 3H; Ar—CH$_3$) 8.48 and 8.68 (s, 3H; C(CH$_3$)$_2$).

EXAMPLE 18

5-Methyl-2-piperidino-7-(β-D-ribofuranosylmethyl)imidazo[1,5-b]pyridazine Hydrochloride A solution of the product of Example 17 (302 mg) in ethanol (16 ml) and 0.6N-HCl (8 ml) was stirred at 80° for 1 h and allowed to cool to room temperature. The mixture was basified by the addition of sodium bicarbonate and partitioned between water and ethyl acetate. The organic phase was washed with brine, dried and the solvent removed under reduced pressure to afford an oil. The oil was dissolved in ethyl acetate (3 ml) and the solution was treated with ethanolic hydrogen chloride. The viscous gum which separated out was crystallized from dichloromethane/ethyl acetate to afford the title compound (163 mg) as solid m.p. 176°–178° (decomp.) τ (250 MHz, DMSO-d$_6$) 1.90 (d, 1H; H-4) 2.80 (d, 1H; H-3) 7.47 (s, 3H; Ar—CH$_3$).

EXAMPLE 19

7-(5′-O-Benzoyl-β-D-ribofuranosylmethyl)-5-methyl-2-piperidinoimidazo[1,5-b]pyridazine, Hydrochloride A solution of the product of Example 6(k) (370 mg) in ethanol (16 ml) and 0.6N-HCl (8 ml) was stirred at 70° C. for 1 h, basified by the addition of sodium bicarbonate and diluted with ethyl acetate. The organic phase was separated, dried and the solvent removed under reduced pressure to afford a viscous oil. The product was taken up in dichloromethane and the solution was treated with excess ethanolic hydrogen chloride and diluted with ethyl acetate to afford the title compound (234 mg) as crystals m.p. 136°-137°. τ (250 MHz; DMSO-d$_6$) 2.00 (d, 1H; H-4) 2.88 (d, 1H; H-3) 7.54 (s, 3H; Ar—CH$_3$) ν$_{max}$ (nujol) 1725 cm$^{-1}$.

EXAMPLE 20

2-Chloro-5-methyl-7-[3',5'-O-(1,1,3,3-tetraisopropyl-disilox-1,3-diyl)-β-D-ribofuranosylmethyl]imidazo[1,5-b]pyridazine A solution of the product of Example 3 (341 mg) and 1,3-dichloro-1,1, 3,3-tetraisopropyldisiloxane (350 μl) in dry pyridine (10 ml) was stirred at room temperature for 4 h and the solvent was removed under reduced pressure. The residue was partitioned between water and ethyl acetate, the organic phase was separated, washed with brine and dried. The solvent was removed under reduced pressure and the residue purified by chromatography on silica gel using dichloromethane:-methanol (19:1) for elution to afford the title compound (510 mg) as a solid m.p. 107°-108° ν$_{max}$ (CHBr$_3$) 3520, 1615, 1532, 1032 cm$^{-1}$ τ (250 MHz; DMSO-d$_6$) 1.81 (d, 1H, H-4) 3.32 (d, 1H; H-3) 7.58 (s, 3H; Ar—CH$_3$).

EXAMPLE 21

7-[2'-O-Benzoyl-3',5'-O-(1,1,3,3-tetraisopropyldisilox-1,3-diyl)-β-D-ribofuranosylmethyl]-2-chloro-5-methylimidazo[1,5-b]pyridazine Dicyclohexylcarbodiimide (221 mg) was added to a solution of benzoic acid (126 mg) and 4-dimethylaminopyridine (16 mg) in dichloromethane (3 ml). The resulting suspension was treated with a solution of the product of Example 20 (410 mg) in dichloromethane (7 ml). The resulting mixture was stirred at room temperature for 2 days. Further additions of benzoic acid (250 mg), and dicyclohexylcarbodiimide (450 mg) were made and the reaction allowed to proceed for a further 7 days. The mixture was filtered and the filtrate concentrated under reduced pressure to a syrup which was purified by chromatography on silica gel using dichloromethane:methanol (19:1) for elution to afford the title compound (419 mg) as a viscous oil ν$_{max}$ (CHBr$_3$) 1720, 1272, 1615, 1605, 1025 cm$^{-1}$ τ (200 MHz; CDCl$_3$) 2.45 (d, 1H; H-4) 3.66 (d, 1H; H-3) 7.58 (s, 3H; Ar—CH$_3$).

EXAMPLE 22

7-(2'-O-Benzoyl-β-D-ribofuranosylmethyl)-2-chloro-5-methylimidazo[1,5-b]pyridazine and
7-(3'-O-Benzoyl-β-D-ribofuranosylmethyl)-2-chloro-5-methylimidazo[1,5-b]pyridazine A solution of the product of Example 21 (364 mg) in tetrahydrofuran (2 ml) was treated with a 1.0M solution of tetra-n-butylammonium fluoride in tetrahydrofuran (2.3 ml) and the mixture was stirred at room temperature for 30 min. The solvent was removed under reduced pressure and the residual gum was shown by thin-layer chromatography to consist of a mixture of two compounds which were separated and purified by chromatography on silica gel using ethyl acetate for elution. Each product was subsequently further purified by crystallization from ether. The more polar product, the first-named title compound, (23 mg) was obtained as a solid m.p. 138°-140° τ (250 MHz; DMSO-d$_6$) 1.98 (d, 1H; H-4) 3.44 (d, 1H; H-3) 7.71 (s, 3H; Ar—CH$_3$) ν$_{max}$ (nujol) 3570-2500, 1730, 1612, 1602 cm$^{-1}$. The less polar product, the second-named title compound, (19 mg) was obtained as a yellow solid m.p. 167°-168° τ (250 MHz; DMSO-d$_6$) 1.79 (d, 1H; H-4) 3.31 (d, 1H; H-3) 7.56 (s, 3H; Ar—CH$_3$) ν$_{max}$ (nujol) 3420, 3340, 1712, 1612, 1278 cm$^{-1}$.

EXAMPLE 23

7-(5'-O-Benzoyl-β-D-ribofuranosylmethyl)-2-chloro-5-methylimidazo[1,5-b]pyridazine The product of Example 1 (560 mg) in ethanol (20 ml) was treated with 0.6N-HCl (10 ml). The resulting solution was stirred at 80° for 1 h, basified by the addition of sodium carbonate and the ethanol was removed under reduced pressure. The residual aqueous mixture was extracted with ethyl acetate and the extracts were dried. The solvent was removed under reduced pressure and the residue recrystallized from ethyl acetate to afford the title compound (420 mg) as crystals m.p. 158°-161° τ (200 MHz; DMSO-d$_6$) 1.91 (d, 1H, H-4) 1.98-2.10 and 2.26-2.54 (m, 5H; PhCO) 3.41 (d, 1H; H-3) 4.95-5.10 (broad, 2H; OH) 5.54-6.14 (m, 6H; H-1', H-2', H-3', H-4' and —CO$_2$CH$_2$—) 6.75-6.86 (m, 2H; homo—CH$_2$—) 7.61 (s, 3H; Ar—CH$_3$).

The hydrochloride salt, prepared by treatment of an ethanolic solution of the above compound with hydrogen chloride, was obtained as a solid m.p. 152°-153° τ (250 MHz; DMSO-d$_6$) 1.62 (d, 1H; H-4) 2.00-2.50 (m, 5H; PhCO) 2.99 (d, 1H; H-3) 5.52-6.14 (m, 6H; H-1', H-2', H-3', H-4' and —CO$_2$CH$_2$—) 6.52-6.63 (m, 2H; homo—CH$_2$—) 7.49 (s, 3H; Ar—CH$_3$).

EXAMPLE 24

2-Chloro-5-methyl-7-[2'-O-octanoyl-3',5'-O-(1,1,3,3-tetraisopropyldisilox-1,3-diyl)-β-D-ribofuranosylmethyl]imidazo[1,5-b]pyridazine Dicyclohexylcarbodiimide (650 mg) was added to a solution of 1-octanoic acid (0.5 ml) and 4-dimethylaminopyridine (18 mg) in dichloromethane (3 ml). A solution of the product of Example 20 (570 mg in dichloromethane (6 ml) was added and the resulting mixture was stirred at room temperature for 20 h and filtered. The filtrate was washed with aqueous sodium bicarbonate and brine, dried and the solvent removed under reduced pressure to afford a syrup which was purified by chromatography on silica gel using dichloromethane:methanol (24:1) for elution to afford the title compound (580 mg) as a viscous oil. ν$_{max}$(CHBr$_3$) 1732, 1615, 1035 cm$^{-1}$ τ (250 MHz; CDCl$_3$) 2.39 (d, 1H; H-4) 3.63 (d, 1H; H-3) 7.55 (s, 3H; Ar—CH$_3$).

EXAMPLE 25

2-Chloro-5-methyl-7-(2'-O-octanoyl-β-D-ribofuranosylmethyl)imidazo[1,5-b]pyridazine and
2-Chloro-5-methyl-7-(3'-O-octanoyl-β-D-ribofuranosylmethyl)imidazo[1,5-b]pyridazine A solution of the product of Example 24 (490 mg) in tetrahydrofuran (3 ml) was treated with a 1.0M solution of tetra-n-butylammonium fluoride in tetrahydrofuran (1.9 ml) and the mixture was stirred at room temperature for 2 min. The solvent was removed under reduced pressure to give a gum which was purified by chromatography on silica gel using ethyl acetate:diethyl ether (3:2) for elution followed by trituration with diethyl ether to give a 7:3 mixture respectively of the title compounds (97 mg) as a solid m.p. 97°-102°.

For the first-named title compound: τ (250 MHz; DMSO-d$_6$) 1.80 (d; H-4) 3.32 (d; H-3) 4.87 (d; 3′—OH) 5.20 (m; H-3′ and 5′—OH) 5.67 (q; H-3′) 5.94 (m; H-1′) 6.30 (q; H-4′) 6.50–6.90 (m; homo—CH$_2$— and 2H-5′) 7.58 (s; Ar—CH$_3$) 7.88 (m; CH$_2$CO$_2$) 8.30–8.90 (m; —(CH$_2$)$_5$) 9.13 (t; alkyl—CH$_3$).

For the second-named title compound: τ (250 MHz; DMSO-d$_6$) 1.80 (d; H-4) 3.32 (d; H-3) 4.69 (d; 3′—OH) 4.97 (t; H-3′) 5.06 (t; 5′—OH) 5.82 (q; H-1′) 5.94 (m; H-2′) 6.18 (q; H-4′) 6.50–6.90 (m; homo—CH$_2$— and 2H-5′) 7.56 (s; Ar—CH$_3$) 7.65 (t; —CH$_2$CO$_2$) 8.30–8.90 (m; —(CH$_2$)$_5$) 9.13 (t; alkyl—CH$_3$).

EXAMPLE 26

5-Methyl-2-piperidino-7-[3′,5′-O-(1,1,3,3-tetraisopropyldisilox-1,3-diyl)-β-D-ribofuranosylmethyl]imidazo[1,5-b]pyridazine A solution of the product of Example 20 (498 mg) in piperidine (10 ml) was stirred under reflux for 3 h and evaporated under reduced pressure to a syrup. The syrup was purified by chromatography on silica gel using dichloromethane:methanol (24:1) for elution to give the title compound (356 mg) as a viscous oil. ν$_{max}$(CHBr$_3$) 3530, 1622, 1036 cm$^{-1}$ τ (250 MHz; CDCl$_3$) 2.58 (d, 1H; H-4) 3.72 (d, 1H; H-3) 7.62 (s, 3H; Ar—CH$_3$).

EXAMPLE 27

7-[2′-O-Benzoyl-3′,5′-O-(1,1,3,3-tetraisopropyldisilox-1,3-diyl)-β-D-ribofuranosylmethyl]-5-methyl-2-piperidinoimidazo[1,5-b]pyridazine Dicyclohexylcarbodiimide (315 mg) was added to a solution of benzoic acid (186 mg) and 4-dimethylaminopyridine (16 mg) in dichloromethane (2 ml). The resulting suspension was treated with a solution of the product of Example 26 (308 mg) in dichloromethane (6 ml) and the mixture was stirred at room temperature for 3 days. Further portions of benzoic acid (120 mg) and dicyclohexylcarbodiimide (210 mg) were added and the reaction stirred for a further 24 h. The mixture was filtered and the filtrate diluted with dichloromethane (50 ml). The solution was washed with aqueous sodium bicarbonate solution and brine, dried and concentrated under reduced pressure to a syrup which was purified by chromatography on silica gel. Elution with dichloromethane:methanol (19:1) afforded the title compound (346 mg) as a viscous oil. ν$_{max}$(CHBr$_3$) 1720, 1621, 1270, 1030 cm$^{-1}$ τ (250 MHz CDCl$_3$) 2.62 (d, 1H; H-4) 3.75 (d, 1H; H-3) 7.62 (s, 3H; Ar—CH$_3$).

EXAMPLE 28

7-(2′-O-Benzoyl-β-D-ribofuranosylmethyl)-5-methyl-2-piperidinoimidazo-[1,5-b]pyridazine and
7-(3′-O-Benzoyl-β-D-ribofuranosylmethyl)-5-methyl-2-piperidinoimidazo[1,5-b]pyridazine A solution of the product of Example 27 (304 mg) in tetrahydrofuran (2 ml) was treated with a 1.0M solution of tetra-n-butylammonium fluoride in tetrahydrofuran (1.0 ml) and the mixture stirred at room temperature for 2 min. The solvent was removed under reduced pressure to a gum which was purified by chromatography on silica gel. Elution with ethyl acetate and subsequent crystallization of the product from ether gave a 1:1 mixture of the title compounds as a solid (93 mg) m.p. 156°–160°.

For the first-named title compound: τ (250 MHz; DMSO-d$_6$) 1.97 (d; H-4) 2.20–2.60 (m; COPh) 3.54 (d; H-3) 4.97 (t; H-2′) 5.52 (q; H-3′) 5.80 (m; H-1′) 6.19 (q; H-4′) 6.30–7.00 (m; homo—CH$_2$—, 2H-5′ and piperidine C-2 and C-6 methylenes) 7.78 (s; Ar—CH$_3$) 8.30–8.60 (m; piperidine C-3, C-4 and C-5 methylenes).

For the second-named title compound: τ (250 MHz; DMSO-d$_6$) 1.97 (d; H-4) 2.20–2.60 (m; COPh) 3.38 (d; H-4) 4.69 (t; H-3′) 5.68 (q; H-1′) 5.80 (m; H-2′) 5.96 (q; H-4′) 6.30–7.00 (m; homo—CH$_2$—, 2H-5′ and piperidine C-2 and C-6 methylenes) 7.67 (s; Ar—CH$_3$) 8.30–8.60 (m; piperidine C-3, C-4 and C-5 methylenes).

The following examples illustrate pharmaceutical formulations according to the invention, containing 7-(5′-O-benzoyl-β-D-ribofuranosylmethyl)-2-chloro-5-methylimidazo[1,5-b]pyridazine hydrochloride as the active ingredient, (109 mg of the hydrochloride contains 100 mg of the free base). Other compounds of the invention may be formulated in a similar manner.

(1) Oral Capsule

| Ingredient | Per Capsule |
|---|---|
| Active Ingredient | 109 mg |
| Lactose Anhydrous | 126 mg |
| Magnesium stearate | 2 mg |
| Sodium starch glycolate | 13 mg |
| Capsule fill weight | 250 mg |

Sieve all the ingredients and mix in a suitable blender. Fill into suitable size hard gelatin capsules using an automatic capsule filling machine.

(2) Oral Tablet

| Ingredient | Per Tablet |
|---|---|
| Active Ingredient | 109 mg |
| Microcrystalline cellulose | 183 mg |
| Sodium starch glycolate | 6 mg |
| Magnesium stearate | 2 mg |
| Tablet weight | 300 mg |

Sieve the active compound and microcrystalline cellulose through a 40 mesh screen. Sieve the sodium starch glycolate and magnesium stearate through a 60 mesh screen. Blend the powders together in a suitable blender until homogeneous. Compress on appropriate punches on an automatic tablet machine. The tablets may be covered in a thin polymer coat applied by the usual film coating techniques. A pigment may be included in the film coat.

(3) Oral Tablet

| Ingredient | Per Tablet |
|---|---|
| Active Ingredient | 109 mg |
| Lactose | 100 mg |
| Maize Starch | 50 |
| Polyvinyl pyrrolidone | 2 |
| Sodium starch glycolate | 7 |
| Magnesium stearate | 2 |
| Tablet weight | 270 |

Sieve the active ingredient and maize starch through a 40 mesh screen. Blend the maize starch with the active ingredient in a suitable blender. Make an aqueous solution of the polyvinyl pyrrolidone in a 5–10% w/v solution. Add this solution to the mixing powders and mix until granulated. Using suitable equipment pass the granulate through a 12 mesh screen. Dry the granules in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine. The tablets may be covered in a thin polymer coat applied by the usual film coating techniques. A pigment may be included in the film coat.

(4) Dry powder for intramuscular injection

Fill the sterile dry powder aseptically into glass vials, the claimed contents of active ingredient being equivalent to 10 mg of free base. Purge the vial headspace with sterile nitrogen and close the vials using rubber plugs and metal overseals (applied by crimping). The suspension may be prepared by adding 1 ml Water for Injections or other suitable vehicle shortly before intramuscular injection.

(5) Inhalation Cartridge

| Ingredient | Per Cartridge |
|---|---|
| Active ingredient micronised | 5 mg |
| Lactose BP to | 25.0 mg |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler.

(6) Suspension aerosol

The active ingredient is micronised to a mean particle size by weight between 1–10 μm in diameter. It is then slurried with a concentrated solution of the appropriate dispersing aid (liquid or solid/ionic or non-ionic surface active agent) in trichlorofluoromethane before being let down into the correct volume of trichlorofluoromethane. The micronised drug is then mixed into the solution with a high shear mixer for a period of not less than 20 minutes. The suspension is metered into aluminium aerosol cans and suitable metering valves, delivering an appropriate amount (e.g 25–200 μl) of suspension are crimped onto the cans. Dichlorodifluoromethane is then pressure filled into the cans through the valves.

(6) Suspension Aerosol

| Ingredients | Per Inhaler wt/g |
|---|---|
| Example a | 100 μg/shot |
| Active Ingredient micronised | 28.8 × 10⁻³ |
| Oleic Acid | 2.88 × 10⁻³ |
| Trichlorofluoromethane | 5.671 |
| Dichlorodifluoromethane | 14.700 |
| Example b | 500 μg/shot |
| Active Ingredient micronised | 0.144 |
| Lecithin | 0.007 |
| Trichlorofluoromethane | 5.632 |
| Dichlorodifluoromethane | 14.600 |
| Example c | 1 mg/shot |
| Active Ingredient micronised | 0.288 |
| Sorbitan Trioleate | 0.222 |
| Trichlorofluoromethane | 5.541 |
| Dichlorodifluoromethane | 14.391 |
| Example d | 10 mg/shot |
| Active Ingredient micronised | 1.679 |
| Sodium dialkyl Sulphosuccinate | 0.034 |
| Trichlorofluoromethane | 5.254 |
| Dichlorodifluoromethane | 13.646 |

We claim:

1. Compounds of the formula:

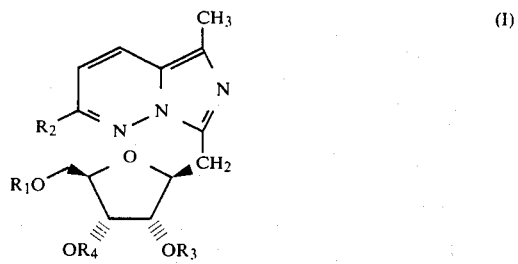

wherein
$R_1$, $R_3$ and $R_4$ are each independently selected from the group consisting of hydrogen atoms and protecting groups;
$R_2$ is selected from the group consisting of halogen atoms and groups of formula —$NR_aR_b$ (where $R_a$ and $R_b$, which may be the same or different, are each selected from hydrogen atoms and alkyl groups; or $R_a$ and $R_b$ may be linked to form, together with the nitrogen atom to which they are attached, a saturated heterocyclic ring which may comprise a further heteroatom selected from the group consisting of nitrogen and oxygen); and their physiological equivalents as well as salts thereof with acids.

2. Compounds of claim 1 wherein one or more of $R_1$, $R_3$ and $R_4$ represents an acyl group of formula RCO wherein R represents a hydrocarbyl group containing up to 30 carbon atoms.

3. Compounds of claim 1 of the formula (Ia):

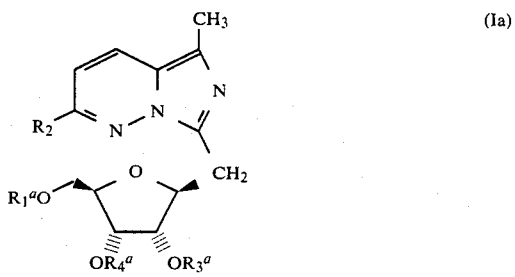

wherein one or more of $R_1{}^a$, $R_3{}^a$ and $R_4{}^a$ represents an acyl group of formula $R^aCO$ where $R^a$ represents a $C_{3-30}$ hydrocarbyl group except that when $R_2$ represents the group $NR_aR_b$, $R_1{}^a$, $R_3{}^a$ and $R_4{}^a$ may additionally all represent hydrogen atoms;

and their physiological equivalents and physiologically acceptable salts.

4. Compounds of claim 3 wherein $R^a$ is selected from the group consisting of straight and branched chain $C_{3-15}$ alkyl groups; alkenyl and alkynyl groups each containing 3–15 carbon atoms; monocyclic $C_{3-7}$ cycloalkyl groups; polycyclic $C_{9-22}$ cycloalkyl groups; $C_{6-14}$ aromatic hydrocarbyl groups; and $C_{7-10}$ aralkyl groups.

5. Compounds of claim 4 wherein $R^a$ is selected from the group consisting of $C_{5-10}$ alkyl, $C_{3-7}$ cycloalkyl, phenyl, naphthyl, adamantyl and phenyl-$C_{1-3}$ alkyl groups.

6. Compounds of claim 1 wherein $R_2$ is chlorine, bromine or a group having formula —$NR_aR_b$ wherein $R_a$ represents a $C_{1-6}$ alkyl group and $R_b$ is hydrogen or $C_{1-3}$ alkyl, or —$NR_aR_b$ represents a pyrrolidino, piperidino, piperazino or morpholino group, each of which may carry one or more C$_{1-2}$ alkyl substituent.

7. Compounds of claim 3 wherein R$^a{}_1$ is R$^a$CO, where R$^a$ is selected from the group consisting of propyl, pentyl, hexyl, heptyl, octyl, cyclohexyl, adamantyl, phenyl, naphthyl and benzyl, and R$_2$ is selected from the group consisting of chlorine, bromine, (C$_{1-6}$ alkyl)amino, dimethylamino, and piperidino.

8. A compound selected from the group consisting of 7-(5'-O-benzoyl-β-D-ribofuranosylmethyl)-2-chloro-5-methylimidazo[1,5-b]pyridazine, physiological equivalents and physiologically acceptable salts thereof.

9. A compound selected from the group consisting of:
7-(5'-O-benzoyl-β-D-ribofuranosylmethyl)-5-methyl-2-(methylamino)imidazo[1,5-b]pyridazine;
2-chloro-5-methyl-7-(5'-O-phenylacetyl-β-D-ribofuranosylmethyl)imidazo[1,5-b]pyridazine;
2-chloro-7-(5'-O-hexanoyl-β-D-ribofuranosylmethyl)-5-methylimidazo[1,5-b]pyridazine;
7-(5'-O-butanoyl-β-D-ribofuranosylmethyl)-2-chloro-5-methylimidazo[1,5-b]pyridazine;
2-chloro-7-[5'-O-(cyclohexanecarbonyl)-β-D-ribofuranosylmethyl]-5-methylimidazo[1,5-b]pyridazine;
7-[5'-O-(1-adamantanecarbonyl)-β-D-ribofuranosylmethyl]-2-chloro-5-methylimidazo[1,5-b]pyridazine;
2-chloro-7-[5'-O-(2-naphthoyl)-β-D-ribofuranosylmethyl]-5-methylimidazo[1,5-b]pyridazine;
7-(5'-O-benzoyl-β-D-ribofuranosylmethyl)-2-(dimethylamino)-5-methylimidazo[1,5-b]pyridazine;
7-(5'-O-benzoyl-β-D-ribofuranosylmethyl)-5-methyl-2-(N-pentylamino)imidazo[1,5-b]pyridazine;
7-(5'-O-benzoyl-β-D-ribofuranosylmethyl)-2-bromo-5-methylimidazo[1,5-b]pyridazine;
2-chloro-7-(5'-O-octanoyl-β-D-ribofuranosylmethyl)-5-methylimidazo[1,5-b]pyridazine;
2-(dimethylamino)-5-methyl-7-(β-D-ribofuranosylmethyl)imidazo[1,5-b]pyridazine;
7-(5'-O-benzoyl-β-D-ribofuranosylmethyl)-5-methyl-2-piperidinoimidazo[1,5-b]pyridazine,
7-(2'-O-benzoyl-β-D-ribofuranosylmethyl)-2-chloro-5-methylimidazo[1,5-b]pyridazine;
7-(3'-O-benzoyl-β-D-ribofuranosylmethyl)-2-chloro-5-methylimidazo[1,5-b]pyridazine;
2-chloro-5-methyl-7-(2'-O-octanoyl-β-D-ribofuranosylmethyl)imidazo[1,5-b]pyridazine;
2-chloro-5-methyl-3'-O-octanoyl-β-D-ribofuranosylmethyl)imidazo[1,5-b]pyridazine;
7-(2'-O-benzoyl-β-d-ribofuranosylmethyl)-5-methyl-2-piperidinoimidazo[1,5-b]pyridazine;
7-(3'-O-benzoyl-β-D-ribofuranosylmethyl)-5-methyl-2-piperidinoimidazo[1,5-]pyridazine;
and physiological equivalents and physiologically acceptable salts thereof.

10. A method for the therapy or prophylaxis of RNA viral infections in a human or animal subject which comprises administering a therapeutic or prophylactic effective amount of one or more compounds selected from the group consisting of compounds of the formula:

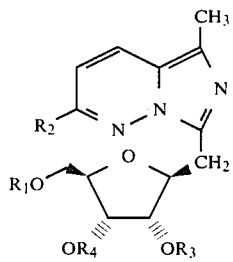

wherein
R$_1$, R$_3$ and R$_4$ are each independently selected from the group consisting of hydrogen atoms and protecting groups;
R$_2$ is selected from the group consisting of halogen atoms and groups of formula —NR$_a$R$_b$ (where R$_a$ and R$_b$, which may be the same or different, are each selected from hydrogen atoms and alkyl groups; or R$_a$ and R$_b$ may be linked to form, together with the nitrogen atom to which they are attached, a saturated heterocyclic ring which may comprise a further heteroatom selected from the group consisting of nitrogen and oxygen);
physiological equivalents thereof, and physiologically acceptable salts thereof with acids.

11. A method for the therapy or prophylaxis of RNA viral infections in a human or animal subject which comprises administering a therapeutic or prophylactic effective amount of one or more of the compounds of claim 9.

12. A method for the therapy or prophylaxis of RNA viral infections in a human or animal subject which comprises administering a therapeutic or prophylactic effective amount of a compound selected from the group consisting of 7-(5'-O-benzoyl-β-D-ribofuranosylmethyl)-2-chloro-5-metylimidazo[1,5-b]pyridazine, physiological equivalents thereof, and physiologically acceptable salts thereof with acids.

13. A pharmaceutical composition comprising one or more compounds selected from the group consisting of compounds of the formula:

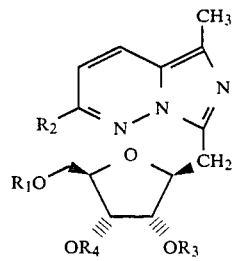

wherein
R$_1$, R$_3$ and R$_{44}$ are each independently selected from the group consisting of hydrogen atoms and protecting groups;
R$_2$ is selected from the group consisting of halogen atoms and groups of formula —NR$_a$R$_b$ (where R$_a$ and R$_b$, which may be the same or different, are each selected from hydrogen atoms and alkyl groups; or R$_a$ and R$_b$ may be linked to form, together with the nitrogen atom to which they are attached, a saturated heterocyclic ring which may comprise a further heteroatom selected from the group consisting of nitrogen and oxygen);
physiological equivalents thereof, and physiologically acceptable salts thereof with acids, in association with a pharmaceutical carrier or excipient adapted for use in human or veterinary medicine.

14. Compounds of formula (II)

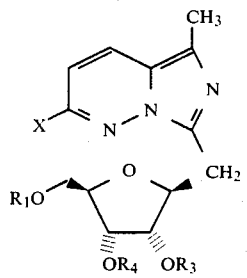
(II)

wherein $R_1$, $R_3$ and $R_4$ are each independently selected from the group consisting of hydrogen atoms and protecting groups; and X is selected from the group consisting of hydroxy and acyloxy.

15. Compounds of formula (III)

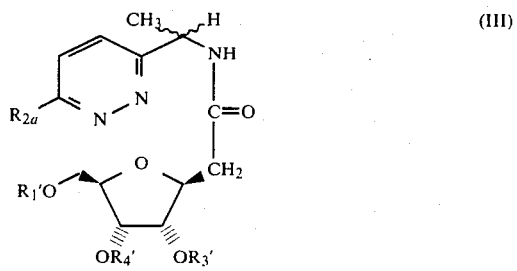
(III)

wherein $R_1'$, $R_3'$ and $R_4'$ are protecting groups and $R_{2a}$ is selected from the group consisting of halogen atoms, hydroxy groups and groups of formula $-NR_aR_b$ (where $R_a$ and $R_b$, which may be the same or different, are each selected from hydrogen atoms and alkyl groups; or $R_a$ and $R_b$ may be linked to form, together with the nitrogen atom to which they are attached, a saturated heterocyclic ring which may comprise a further heteroatom selected from the group consisting of nitrogen and oxygen).

* * * * *